(12) United States Patent
Rao et al.

(10) Patent No.: US 8,034,621 B2
(45) Date of Patent: Oct. 11, 2011

(54) CHEMICAL SENSORS OF ZINC, NICKEL, AND COPPER IONS

(75) Inventors: Chebrolu Pulla Rao, Mumbai (IN); Roymon Joseph, Mumbai (IN)

(73) Assignee: Indian Institute of Technology, Mumbai (IN)

( * ) Notice: Subject to any disclaimer, the term of this patent is extended or adjusted under 35 U.S.C. 154(b) by 93 days.

(21) Appl. No.: 12/543,348

(22) Filed: Aug. 18, 2009

(65) Prior Publication Data

US 2011/0045597 A1 Feb. 24, 2011

(51) Int. Cl.
*G01N 33/20* (2006.01)
*C07D 401/12* (2006.01)
*C07F 15/00* (2006.01)

(52) U.S. Cl. ............... 436/80; 436/81; 436/84

(58) Field of Classification Search .............. 436/91, 436/106, 115, 149, 80, 81, 84; 546/2, 264
See application file for complete search history.

(56) References Cited

OTHER PUBLICATIONS

Roymon, J. et al., "Fluorescence switch-on sensor for $Cu^{2+}$ by an amide linked lower reim 1,3-bis(2-picolyl)amine derivative of calyx[4]arene in aqueous methanol," Tetrahedron Letters, vol. 50, pp. 2735-2739 (2009).

Roymon, J. et al., "Lower rim 1,3-di-amide-derivative of calix[4]arene possessing bis-{N-(2,2'-dipyridylamide)} pendants: a dual fluorescence sensor for $Zn^{2+}$ and $Ni^{2+}$," Tetrahedron Letters, vol. 49, pp. 6257-6261 (2008).

*Primary Examiner* — Jill Warden
*Assistant Examiner* — Dwan A Gerido
(74) *Attorney, Agent, or Firm* — Foley & Lardner LLP

(57) ABSTRACT

The present technology provides a dual chemical sensor for zinc and nickel ions and a chemical sensor for copper ions. Also provided are methods of making and using the chemical sensors. The chemical sensors have the structure of formula I, wherein $R^1$, and $R^2$ are defined as set forth herein.

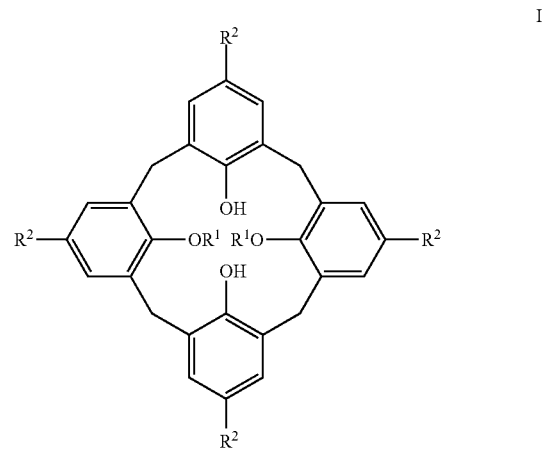

20 Claims, 18 Drawing Sheets

CHEMICAL SENSORS OF ZINC, NICKEL, AND COPPER IONS

BACKGROUND

Zinc, nickel and copper are metals that are necessary in trace amounts for proper functioning of various metalloenzymes in humans and animals. For example, zinc deficiency may be associated with anorexia, impaired immune, neural and reproductive functions. Nickel may act as a co-factor for the absorption of iron in the intestine, and copper deficiencies may lead to neurological problems. However, high levels of these metals are also deleterious to human and animal health.

Overdoses of zinc and some of its compounds such as oxides, sulfates, sulfides and chlorides may cause effects in the respiratory tract such as bronchopneumonia and pneumonitis, developmental defects, inflammatory reactions and even death. Prolonged oral exposure to zinc may cause reduced absorption of copper. Estimates of the minimal risk levels of zinc may range from 77-600 mg/m$^3$ for inhalation and 0.3 mg/kg/day for oral exposure.

Like other heavy metals, nickel overexposure may be associated with a wide variety of toxic effects. Acute effects of nickel toxicity may include respiratory distress and hematuria. Whereas subchronic nickel exposure may lead to hepatic and renal toxicity, chronic nickel exposure may cause adenocarcinoma, immune suppression, genotoxicity and neurotoxicity.

Thus, simple, sensitive and accurate methods for assessing low levels of zinc, nickel, copper in both biological and other sample types are important.

SUMMARY

In one aspect of the present technology, there is provided a compound of Formula I:

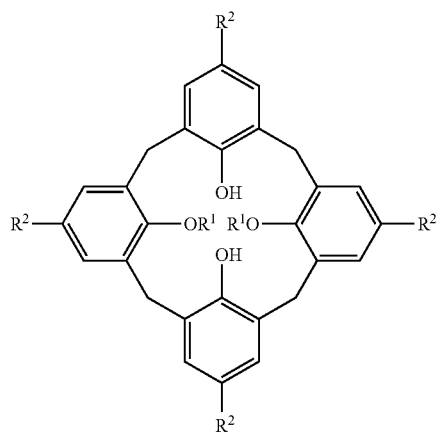

I or salts thereof, wherein
each R$^1$ independently is

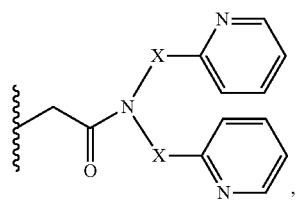

wherein X is —CH$_2$— or is absent, and each R$^2$ is independently a C$_{3-6}$ straight, branched or cyclic alkyl group.

In some embodiments, each R$^2$ is a methyl, ethyl, isopropyl, n-butyl, t-butyl, cyclopropyl, cyclobutyl, cyclopentyl or cyclohexyl group.

In some embodiments, each R$^2$ is a t-butyl.

In some embodiments, X is CH$_2$. In some embodiments, X is absent.

In some embodiments, there is provided a complex of a compound of the invention and Zn$^{2+}$ ion.

In some embodiments, there is provided a complex of a compound of the invention and Ni$^{2+}$ ion.

In some embodiments, there is provided a complex of a compound of the invention and Cu$^{2+}$ ion.

In another aspect, there is provided a method of testing a sample for the presence of Zn$^{2+}$ ions, Ni$^{2+}$ ions, or mixture thereof. The method includes combining a compound of formula I, wherein X is absent, with a test sample; and detecting the fluorescence of the test sample; wherein an increase in the fluorescence of the test sample upon combination with the compound of formula I indicates the presence of Zn$^{2+}$ ion in the test sample and a decrease in the fluorescence of the test sample upon combination with a compound of formula I indicates the presence of Ni$^{2+}$ in the test sample. In some embodiments, the method further includes comparing the detected fluorescence of the test sample with the fluorescence of a control sample, wherein an increase in the fluorescence of the test sample relative to the control sample indicates the presence of Zn$^{2+}$ ion in the test sample and a decrease in the fluorescence of the test sample relative to the control sample indicates the presence of Ni$^{2+}$ in the test sample. In some embodiments, the control sample includes substantially the same amount of the compound of formula I as the test sample but lacks Zn$^{2+}$ and Ni$^{2+}$.

In some embodiments, the concentration of Zn$^{2+}$ ion that can be detected is at least about 140 ppb in the test sample.

In some embodiments, a concentration of Ni$^{2+}$ ion that can be detected is at least about 200 ppb in the test sample.

In some embodiments, the test sample or the control sample is an alcoholic solution.

In some embodiments, the alcoholic solution is methanol or ethanol.

In some embodiments, the method selectively detects the presence of Zn$^{2+}$ ions or Ni$^{2+}$ ions in the presence of one or more additional divalent metal ions.

In some embodiments, the one or more additional divalent metal ions are selected from the group consisting of Co$^{2+}$, Cd$^{2+}$, Cu$^{2+}$, Fe$^{2+}$, Hg$^{2+}$, and Mn$^{2+}$.

In some embodiments of the method, the test sample includes a mixture of Ni$^{2+}$ and Zn$^{2+}$ ions in which the amount of Ni$^{2+}$ ions is at least ten times the amount of Zn$^{2+}$ ions or the amount of Zn$^{2+}$ ions is at least ten times the amount of Ni$^{2+}$ ions.

In yet another aspect, there is provided a method of testing a sample for the presence of Cu$^{2+}$ ions. The method includes combining a compound of formula I, wherein X is CH$_2$, with a test sample; and detecting the fluorescence of the test sample; wherein an increase in the fluorescence of the test sample upon combination with the compound of formula I indicates the presence of Cu$^{2+}$ ion in the test sample.

In some embodiments, the method further includes comparing the detected fluorescence of the test sample with a fluorescence of a control sample, wherein an increase in the fluorescence of the test sample relative to the control sample indicates the presence of $Cu^{2+}$ ion in the test sample.

In some embodiments, the control sample includes substantially the same amount of the compound as the test sample but lacks $Cu^{2+}$.

In some embodiments, a concentration of $Cu^{2+}$ ion that can be detected is at least about 196 ppb in the test sample.

In some embodiments, the test sample or the control sample is an alcoholic solution.

In some embodiments, the alcoholic solution is methanol or a mixture of methanol and water.

In some embodiments, the method selectively detects the presence of $Cu^{2+}$ ion in the presence of one or more additional mono- or divalent metal ions.

In some embodiments, the one or more additional divalent metal ions are selected from the group consisting of $Na^+$, $K^+$, $Ca^{2+}$, $Mg^{2+}$, $Mn^{2+}$, $Co^{2+}$, $Fe^{2+}$, $Hg^{2+}$, $Ni^{2+}$, $Zn^{2+}$, and $Mn^{2+}$.

In another aspect, there is provided a method for preparing a compound of the invention by contacting 2,2'-dipyridylamine or bis(pyridin-2-ylmethyl)amine in a presence of a suitable base and a solvent with a compound of Formula II:

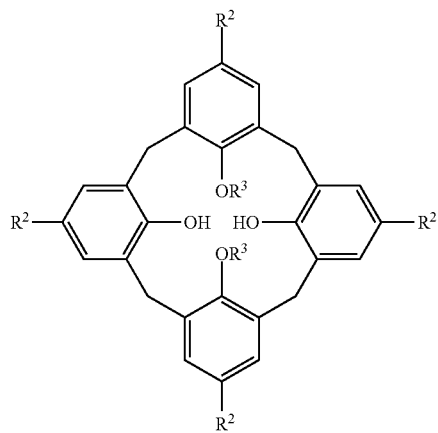

II wherein $R^3$ is —$CH_2COX$ and X is a halide.

In some embodiments, the suitable base is a tertiary amine or a pyridine compound.

In some embodiments, the suitable base is selected from the group consisting of triethylamine, diisopropylethylamine, pyridine, and dimethylaminopyridine.

In some embodiments, the solvent is tetrahydrofuran, diethylether, acetonitrile, carbon tetrachloride, dimethyl sulfoxide, dimethylformamide, or dioxane.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

Figure 1:
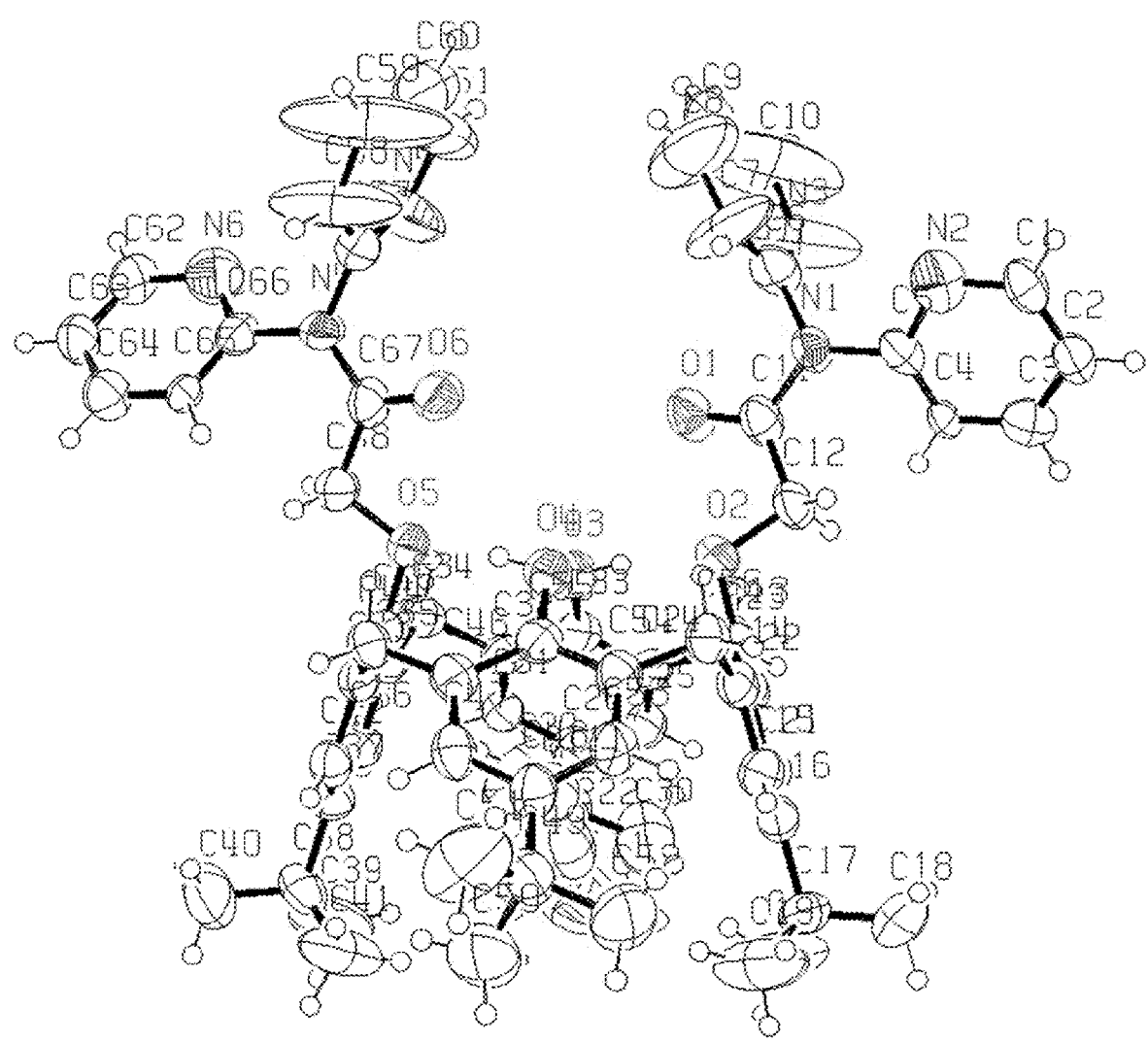
FIG. 1 depicts an illustrative embodiment of an ORTEP (Oak Ridge Thermal Ellipsoid Program) diagram of bis-{N-(2,2'-dipyridylamide)} derivative of calix[4]arene (compound VIII). Hydrogen and solvent molecules are not shown for clarity.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

1. Definitions

The term "alcoholic solution" refers to any solution comprising a $C_{1-10}$ alcohol. In some embodiments the alcoholic solution comprises a $C_{1-8}$, $C_{1-6}$ or a $C_{1-4}$ alcohol. Examples of alcohol include, without limitation, methanol, ethanol, i-propanol, n-propanol, etc.

The term "alkyl" refers to saturated monovalent hydrocarbyl groups having from 1 to 10 carbon atoms, in some embodiments from 1 to 5 carbon atoms, and in some embodiments 1 to 3 carbon atoms. $C_{x-y}$ alkyl refers to alkyl groups having from x to y carbon atoms. This term is exemplified by groups such as methyl, ethyl, n-propyl, iso-propyl, n-butyl, t-butyl, n-pentyl, and the like.

The term "base" refers to a chemical that can donate a pair of electrons or donate a hydroxide ion. Examples of base include, but are not limited to, tertiary amine, pyridine compound etc.

The terms "cyclic alkyl" or "cycloalkyl" refers to a saturated or partially saturated non-aromatic cyclic alkyl groups of from 3 to 14 carbon atoms and no ring heteroatoms and having a single ring or multiple rings including fused and bridged ring systems. For multiple ring systems having aromatic and non-aromatic rings that have no ring heteroatoms, the term "cyclic alkyl" applies when the point of attachment is at a non-aromatic carbon atom (e.g. 5,6,7,8,-tetrahydronaphthalene-5-yl). The term "cyclic alkyl" includes cycloalkenyl groups. Examples of cyclic alkyl groups include, for instance, cyclopropyl, cyclobutyl, cyclopentyl, cyclohexyl, cyclooctyl, and cyclohexenyl. $C_{u-v}$ cyclic alkyl refers to cycloalkyl groups having u to v carbon atoms.

The term "divalent metal ion" refers to any metal ion with a valency of 2. Examples of divalent ions include, but are not limited to, $Zn^{2+}$, $Ni^{2+}$, $Co^{2+}$, $Cu^{2+}$, $Fe^{2+}$, $Hg^{2+}$, $Mn^{2+}$ etc.

The term "halide" refers to chloro, bromo, fluoro, and iodo.

The term "pyridine compound" refers to any compound containing pyridine, such as, but not limited to, pyridine, dimethylaminopyridine, diethylaminopyridine, di-isopropylaminopyridine, etc.

Compounds of the present technology may form salts with inorganic or organic acids. Thus, salts of the present compounds, include but are not limited to, salts of HCl, $H_2SO_4$, and $H_3PO_4$, as well as acetic acid or trifluoroacetic acid. Suitable salts include those described in P. Heinrich Stahl, Camille G. Wermuth (Eds.), Handbook of Pharmaceutical Salts Properties, Selection, and Use; 2002.

The term "solvent" refers to any aprotic solvent. Examples of solvent include, but are not limited to, tetrahydrofuran, diethylether, acetonitrile, carbon tetrachloride, dimethyl sulfoxide, dimethylformamide, or dioxane.

The term "tertiary amine" refers to a tri-substituted amine group. Examples of tertiary amine include, but are not limited to, triethylamine, diisopropylethylamine, etc.

The term "test sample" refers to any sample which is to be tested for the presence of an analyte. In methods of the present technology, the analytes to be detected include metal ions such as zinc, nickel and copper ions.

2. Compounds

In one aspect of the present technology, there is provided a calix[4]arene derivative containing one or more of N-2,2' dipyridylamide groups on the lower rim. The calix[4]arene derivative of the present technology detects zinc and nickel ions by a change in its fluorescence emission in a solution. Binding of zinc to this calix[4]arene derivative results in an increase in the fluorescence emission (switch-on) and binding of nickel to this calix[4]arene derivative results in a decrease in the fluorescence emission (switch-off). Therefore, the calix [4]arene derivative containing at least two N-2,2' dipyridylamide groups of the present technology acts as a dual sensor for zinc and nickel ions.

In another aspect of the present technology, there is provided a calix[4]arene derivative containing one or more of bis(2-picolyl) amine groups on the lower rim. This calix[4] arene derivative of the present technology detects copper ions by a change in its fluorescence emission in a solution. Binding of copper to this calix[4]arene derivative results in an increase in the fluorescence emission (switch-on). Therefore, the calix

[4]arene derivative containing at least two bis(2-picolyl) amine groups of the present technology acts as a sensor for copper ions.

The calix[4]arene derivative of the present technology can be used to detect a level of the zinc, nickel, and/or copper in samples such as, but not limited to, environmental samples such as soil, stone, rock, air, water, etc.; biological samples such as blood, cell, tissue, sweat, etc.; and nutritional samples such as food.

Accordingly, in some embodiments of the present technology there is provided a compound of Formula I:

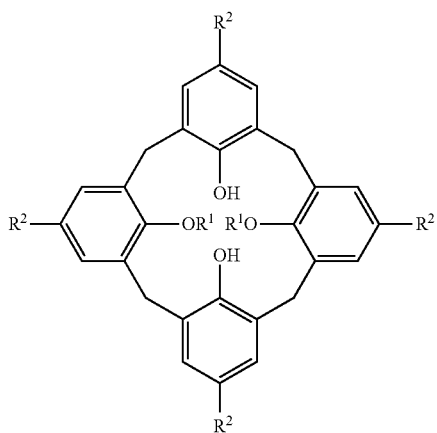

or salts thereof, wherein
each $R^1$ independently is hydrogen or

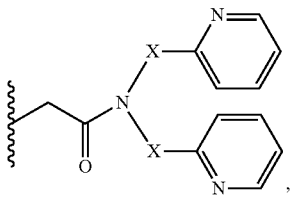

wherein X is —$CH_2$— or is absent, and each $R^2$ is independently a $C_{3-6}$ straight, branched or cyclic alkyl group.

In some embodiments of the compound of formula I, each $R^2$ is a methyl, ethyl, isopropyl, n-butyl, t-butyl, cyclopropyl, cyclobutyl, cyclopentyl or cyclohexyl group. In some embodiments, each $R^2$ is a t-butyl.

In some embodiments of the compound of formula I, X is absent. In other embodiments, X is $CH_2$.

In some embodiments, there is provided a complex of a compound of formula I with a $Zn^{2+}$ ion, wherein X is absent from the compound of formula I. In yet another embodiment, there is provided a complex of a compound of formula I with a $Ni^{2+}$ ion, wherein X is absent from the compound of formula I. In some embodiments, there is provided a complex of a compound of formula I with a $Cu^{2+}$ ion, wherein X is $CH_2$ in the compound of formula I.

In yet another embodiment, there is provided a complex of a compound of formula I with a mixture of $Zn^{2+}$ ion and $Ni^{2+}$ ion. wherein X is absent from the compound of formula I.

In some embodiments, the compound of formula I, wherein X is absent, exhibits changes in fluorescence in the presence of $Zn^{2+}$ ion or $Ni^{2+}$ ion. In some embodiments, the compound of formula I, wherein X is absent, exhibits little or no change in fluorescence in the presence of any divalent metal ion other than $Zn^{2+}$ ion or $Ni^{2+}$ ion. In some embodiments, the compound of formula I, wherein X is absent, exhibits little or no change in fluorescence in the presence of a divalent metal ion such as, $Co^{2+}$, $Cu^{2+}$, $Fe^{2+}$, $Hg^{2+}$, and $Mn^{2+}$.

In some embodiments where the test sample includes a mixture of $Zn^{2+}$ ions and $Ni^{2+}$ ions, the $Ni^{2+}$ ions can be measured when $Zn^{2+}$ ion concentration in the sample is less by at least an order of magnitude than that of $Ni^{2+}$ ion concentration. In some embodiments, the $Zn^{2+}$ can be detected in the sample when the $Ni^{2+}$ concentration is less by at least an order of magnitude than that of $Zn^{2+}$ ion concentration.

3. Method of Use

In another aspect of the present technology, there are provided methods of testing for the presence of $Zn^{2+}$ ions, $Ni^{2+}$ ions, or a mixture thereof in a test sample using compounds of the present technology. In some embodiments, the present technology provides methods of testing a sample for the presence of a $Zn^{2+}$ ion, a $Ni^{2+}$ ion, or mixture thereof including:

combining a compound of formula I, where X is absent, with a test sample, and
detecting the fluorescence of the test sample,
wherein an increase in the fluorescence of the test sample upon combination with the compound of formula I indicates the presence of $Zn^{2+}$ ion in the test sample and a decrease in the fluorescence of the test sample upon combination with the compound of formula I indicates the presence of $Ni^{2+}$ in the test sample.

The methods of the present technology can be used to detect the presence of $Zn^{2+}$ ions, $Ni^{2+}$ ions, or mixture thereof in any test sample. In some embodiments, the test sample is biological sample including, but not limited to, blood, cells, tissue, saliva, sweat, extracts of any of the foregoing, and the like. In some embodiments, the test sample is a nutritional samples including, but not limited to, a drink, food, and extracts thereof. In some embodiments, the test sample is an environmental sample including, but not limited to, water (including surface water or underground water), and extracts and filtrates of air, soil, sediment, clay, and the like.

In some embodiments, the test sample and the control samples are alcoholic solutions such as, but not limited to, solutions including methanol, ethanol, or i-propanol. In some embodiments, the test sample or the control sample is an aqueous alcoholic solution with, e.g., up to 10 to 20% water (by volume). In some embodiments, the test sample and the control sample are methanol solutions.

In the present methods, the compound of formula I and the test sample may be combined in several ways. In some embodiments of the present methods, the compound of formula I may be added to the test sample as a solid or as a solution. Alternatively, the test sample or an aliquot thereof may be added to the compound of formula I or to a solution thereof. The test sample may also be prepared by adding the compound of formula I or a solution thereof and an aliquot of the sample to be tested to a third solution.

In some embodiments of the present methods, the compound of formula I and/or the test sample is in an alcoholic solution including, but not limited to, methanol. It will be understood that other alcohols, as well as water and mixtures thereof may be used in the present methods. It is within the skill in the art to select which alcohols, mixtures thereof or aqueous solutions thereof are to be used in the present methods based on the sample type, sensitivity needed, etc.

In some embodiments, such as those in which the amount of $Zn^{2+}$ or $Ni^{2+}$ ions are to be quantified, the methods further include comparing the detected fluorescence of the test sample with the fluorescence of a control sample, wherein an increase in the fluorescence of the test sample relative to the control sample indicates the presence of $Zn^{2+}$ ion in the test sample and a decrease in the fluorescence of the test sample relative to the control sample indicates the presence of $Ni^{2+}$ in the test sample. In some embodiments of the present methods, the control sample comprises substantially the same amount of compound of formula I as the test sample but lacks $Zn^{2+}$ and $Ni^{2+}$ ions. By "substantially the same amount of compound" in the present context is meant an amount of compound that is the same or sufficiently similar to the amount used in the test sample to allow measurement of the change in fluorescence due primarily to the binding of the $Zn^{2+}$ or $Ni^{2+}$ ions. It is to be understood that a standard concentration curve may be constructed by measuring the fluorescence of known amounts of $Zn^{2+}$ or $Ni^{2+}$ ions in the presence of the same amount of a compound of formula I. Measurement of the fluorescence of the compound of formula I in a test sample having an unknown amount of $Zn^{2+}$ or $Ni^{2+}$ ions, and comparison to such a standard concentration curve allows for quantification of the $Zn^{2+}$ and $Ni^{2+}$ ions.

In some embodiments, the concentration of $Zn^{2+}$ ion that can be detected is at least about 140 ppb in the test sample; or at least about 142 ppb; or at least about 200 ppb; or at least about 300 ppb; or at least about 400 ppb; or at least about 500 ppb in the test sample. In some embodiments, the concentration of $Zn^{2+}$ ion that can be detected is in the range of about 140 ppb to 1000 ppb; or about 140 ppb to about 800 ppb; or about 200 ppb to about 700 ppb; or about 300 ppb to about 600 ppb; or about 400 ppb to about 500 ppb; or about 140 ppb to about 500 ppb; or about 140 ppb to about 300 ppb.

In some embodiments, the concentration of $Ni^{2+}$ ion that can be detected is at least about 200 ppb; or at least about 203 ppb; or at least about 300 ppb; or at least about 341 ppb, or at least about 400 ppb; or at least about 500 ppb in the test sample. In some embodiments, the concentration of $Ni^{2+}$ ion that can be detected is in the range of about 200 ppb to 1000 ppb; or about 200 ppb to about 800 ppb; or about 200 ppb to about 700 ppb; or about 300 ppb to about 600 ppb; or about 400 ppb to about 500 ppb; or about 200 ppb to about 500 ppb; or about 200 ppb to about 400 ppb.

In some embodiments, the method selectively detects the presence of $Zn^{2+}$ ion or $Ni^{2+}$ ion in the presence of one or more additional divalent metal ions. In some embodiments, the one or more additional divalent metal ions are selected from the group consisting of $Co^{2+}$, $Cd^{2+}$, $Cu^{2+}$, $Fe^{2+}$, $Hg^{2+}$, and $Mn^{2+}$.

In some embodiments, the present technology provides methods of testing a sample for the presence of $Cu^{2+}$ ions, by:

combining a compound of formula I, where X is $CH_2$, with a test sample, and detecting the fluorescence of the test sample, wherein an increase in the fluorescence of the test sample upon combination with the compound of formula I indicates the presence of $Cu^{2+}$ ions in the test sample.

The methods of the present technology can be used to detect the presence of $Cu^{2+}$ ions in any test sample. In some embodiments, the test sample is biological sample including, but not limited to, blood, cells, tissue, saliva, sweat, extracts of any of the foregoing, and the like. In some embodiments, the test sample is a nutritional samples including, but not limited to, a drink, food, and extracts thereof. In some embodiments, the test sample is an environmental sample including, but not limited to, water (including surface water or underground water), and extracts and filtrates of air, soil, sediment, clay, and the like.

In some embodiments, the test sample and the control samples are alcoholic solutions such as, but not limited to, solutions including methanol, ethanol, or i-propanol. In some embodiments, the test sample and the control sample are an aqueous alcoholic solution with, e.g., up to 10 to 60% water (by volume). In some embodiments, the test sample and control samples are aqueous solutions such as a 1:1 methanol/water solution.

In the present methods, the compound of formula I and the test sample may be combined in several ways as provided above.

In some embodiments, such as those in which the amount of $Cu^{2+}$ ions are to be quantified, the methods further include comparing the detected fluorescence of the test sample with the fluorescence of a control sample, wherein an increase in the fluorescence of the test sample relative to the control sample indicates the presence of $Cu^{2+}$ ions in the test sample. In some embodiments of the present methods, the control sample comprises substantially the same amount of compound of formula I as the test sample but lacks $Cu^{2+}$ ions. By "substantially the same amount of compound" in the present context is meant an amount of compound that is the same or sufficiently similar to the amount used in the test sample to allow measurement of the change in fluorescence due primarily to the binding of the $Cu^{2+}$ ions. It is to be understood that a standard concentration curve may be constructed by measuring the fluorescence of known amounts of $Cu^{2+}$ ions in the presence of the same amount of a compound of formula I. Measurement of the fluorescence of the compound of formula I in a test sample having an unknown amount of $Cu^{2+}$ ions, and comparison to such a standard concentration curve allows for quantification of the $Cu^{2+}$ ions.

In some embodiments, the concentration of $Cu^{2+}$ ion that can be detected is at least about 196 ppb; or at least about 200 ppb; or at least about 300 ppb; or at least about 341 ppb; or at least about 400 ppb; or at least about 500 ppb in the test sample. In some embodiments, the concentration of $Cu^{2+}$ ion that can be detected is in the range of about 190 ppb to 1000 ppb; or about 190 ppb to about 800 ppb; or about 200 ppb to about 700 ppb; or about 300 ppb to about 600 ppb; or about 400 ppb to about 500 ppb; or about 200 ppb to about 500 ppb; or about 200 ppb to about 400 ppb.

In some embodiments, the method selectively detects the presence of $Cu^{2+}$ ion in the presence of one or more additional mono- or divalent metal ions. In some embodiments, the one or more additional metal ions are selected from the group consisting of $Na^+$, $K^+$, $Ca^{2+}$, $Mg^{2+}$, $Mn^{2+}$, $Co^{2+}$, $Fe^{2+}$, $Hg^{2+}$, $Ni^{2+}$, $Zn^{2+}$, and $Mn^{2+}$. In some embodiments, the method selectively detects the presence of $Cu^{2+}$ ion in the presence of one or more additional mono- or divalent metal ions.

In some embodiments, the metal ion binding properties of calix[4]arene derivative of the present technology are studied by techniques including, but not limited to, fluorescence spectroscopy, absorption spectroscopy, and/or ESI mass spectrometry. Fluorescence of a compound of formula I may be detected by essentially any suitable fluorescence detection device. Such devices are typically comprised of a light source for excitation of the fluorophore and a sensor for detecting emitted light. In addition, fluorescence detection devices may contain a means for controlling the wavelength of the excitation light and a means for controlling the wavelength of the light detected by the sensor. Such means are referred to generically as filters and can include diffraction gratings, dichroic mirrors, or filters. Examples of suitable devices include fluorometers, spectrofluorometers and fluorescence microscopes. Many such devices are commercially available from companies such as Perkin-Elmer, Hitachi, Nikon, Molecular Dynamics, or Zeiss. In certain embodiments, the device is coupled to a signal amplifier and a computer for data processing. Examples of absorption spectroscopy include, but are not limited to, infrared spectroscopy, microwave spectroscopy, and UV-visible spectroscopy.

4. Methods of Preparation

The compounds of this technology can be prepared from readily available starting materials using, for example, the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts (1999) *Protecting Groups in Organic Synthesis,* 3rd Edition, Wiley, New York, and references cited therein.

Furthermore, the compounds of this technology may contain one or more chiral centers. Accordingly, if desired, such compounds can be prepared or isolated as pure stereoisomers, i.e., as individual enantiomers or diastereomers, or as stereoisomer-enriched mixtures. All such stereoisomers (and enriched mixtures) are included within the scope of this technology, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents, and the like.

The starting materials for the following reactions are generally known compounds or can be prepared by known procedures or obvious modifications thereof. For example, many of the starting materials are available from commercial suppliers such as Aldrich Chemical Co. (Milwaukee, Wis., USA), Bachem (Torrance, Calif., USA), Emka-Chemce or Sigma (St. Louis, Mo., USA). Others may be prepared by procedures, or obvious modifications thereof, described in standard reference texts such as Fieser and Fieser's Reagents for Organic Synthesis, Volumes 1-15 (John Wiley, and Sons, 1991), Rodd's Chemistry of Carbon Compounds, Volumes 1-5, and Supplementals (Elsevier Science Publishers, 1989), Organic Reactions, Volumes 1-40 (John Wiley, and Sons, 1991), March's Advanced Organic Chemistry, (John Wiley, and Sons, 5$^{th}$ Edition, 2001), and Larock's Comprehensive Organic Transformations (VCH Publishers Inc., 1989).

The compounds of formula I may be prepared by, for example, the synthetic protocol illustrated in Scheme 1.

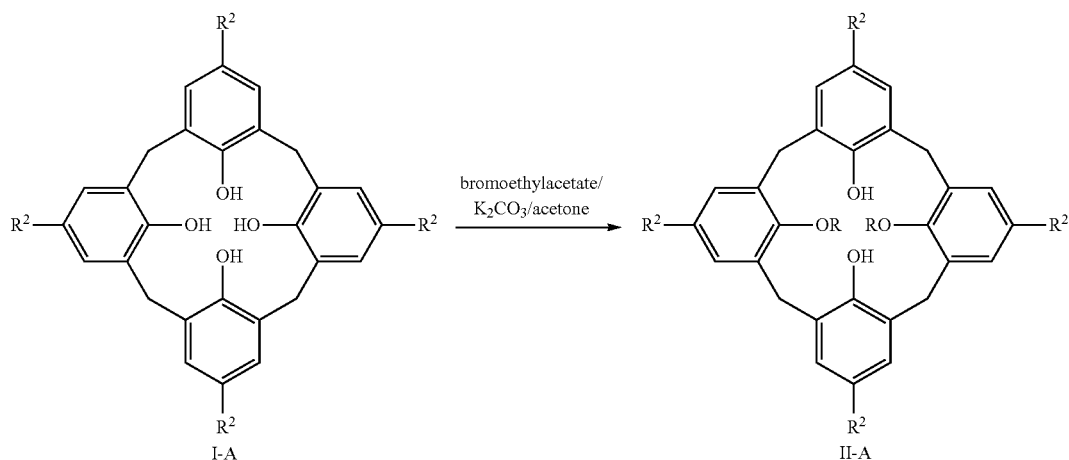

-continued

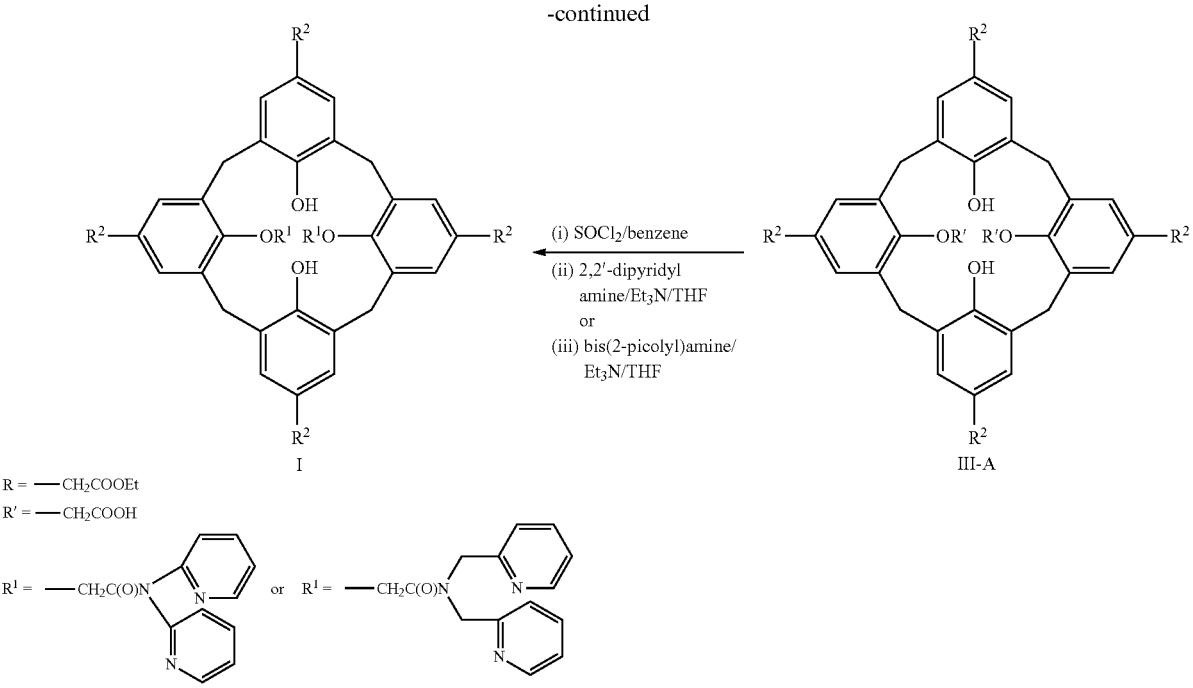

In Scheme 1, the substituents $R^1$ and $R^2$ are as defined herein. p-Substituted calix[4]arene I-A can be purchased from commercial sources. The compound of formula I-A may be reacted with bromoethyl acetate in the presence of a suitable base to produce ester II-A. Example of such bases include, but are not limited to, potassium carbonate, potassium bicarbonate, sodium hydroxide, potassium hydroxide, etc. Upon reaction completion, compounds of Formula II-A can be recovered by conventional techniques such as neutralization, extraction, precipitation, chromatography, filtration, and the like. In some embodiments, the compounds of Formula II-A are purified using high-performance liquid chromatography. In some embodiments, the compounds of Formula II-A are used as is in the next reaction.

Ester hydrolysis of II-A in the presence of the suitable base and an alcohol results in acid III-A. Example of alcohol includes, but is not limited to, ethanol, methanol, i-propanol, etc. The reaction may be heated or refluxed, if desired. Upon reaction completion, compounds of Formula III-A can be recovered by conventional techniques such as neutralization, extraction, precipitation, chromatography, filtration, and the like. In some embodiments, the compounds of Formula III-A are purified using high-performance liquid chromatography. In some embodiments, the compounds of Formula III-A are used as is in the next reaction.

The acid III-A can then be subjected to chlorination by, e.g., treatment with thionyl chloride in the presence of a suitable solvent to give the acid chloride (not shown in the scheme). The reaction may be heated or refluxed, if desired. It is to be understood that other chlorinating agents known in the art can also be used in this reaction, such as but not limited to, phosphorus trichloride ($PCl_3$), and phosphorus pentachloride ($PCl_5$). Upon reaction completion, the acid chloride can be recovered by conventional techniques such as neutralization, extraction, precipitation, chromatography, filtration, and the like. In some embodiments, the acid chloride is purified using high-performance liquid chromatography. In some embodiments, the acid chloride is used as is in the next reaction.

The acid chloride is then treated with an amine derivative in the presence of a suitable base and a solvent to result in compounds of formula I. The amine derivatives include 2,2'-dipyridyl amine or bis-(2-picolyl amine). Examples of base include, but are not limited to, tertiary amines or a pyridine compound, such as, triethylamine, diisopropylethylamine, pyridine, and dimethylaminopyridine. Examples of solvent include, but are not limited to, tetrahydrofuran, diethylether, acetonitrile, carbon tetrachloride, dimethyl sulfoxide, dimethylformamide, or dioxane.

Upon reaction completion, compounds of Formula I can be recovered by conventional techniques such as neutralization, extraction, precipitation, chromatography, filtration, and the like. In some embodiments, the compounds of Formula I are purified using high-performance liquid chromatography.

It is to be understood that the synthetic method in Scheme I, where the two R, R' or $R^1$ groups are opposite to each other, is for illustration purposes only and other deviations or modifications from the scheme to result in the compounds of formula I are well within the skill of a person of ordinary skill in the art.

Thus, in one aspect of the present technology, there is provided a method for preparing a compound of the present technology by contacting 2,2'-dipyridylamine or bis(pyridin-2-ylmethyl)amine in a presence of a suitable base and a solvent with a compound of Formula II:

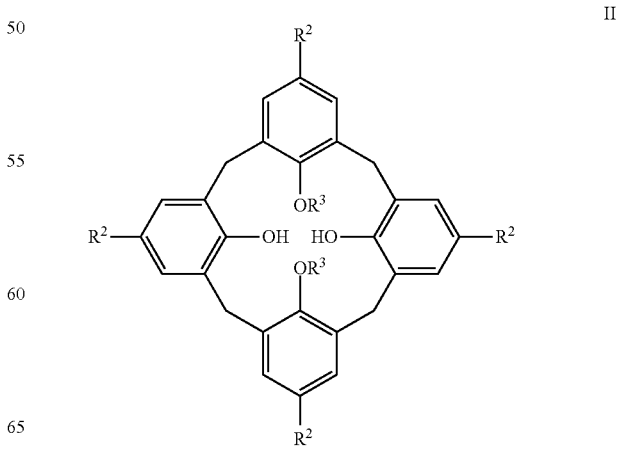

wherein $R^3$ is —$CH_2COX$ and X is a halide.

In some embodiments, the suitable base is a tertiary amine or a pyridine compound. In some embodiments, the suitable base is selected from the group consisting of triethylamine, diisopropylethylamine, pyridine, and dimethylaminopyridine.

In some embodiments, the solvent is tetrahydrofuran, diethylether, acetonitrile, carbon tetrachloride, dimethyl sulfoxide, dimethylformamide, or dioxane.

EXAMPLES

The present technology is further illustrated by the following examples, which should not be construed as limiting in any way. The following definitions are used herein.

Å Angstrom
$CHCl_3$ Chloroform
$CH_3OH$ Methanol
d Doublet
ESI Electron spray ionization
FTIR Fourier transform infra-red
g Gram
MHz Megahertz
μL Microliter
mL Milliliter
μM Micromolar
MP Melting point
MS Mass spectroscopy
m/z Mass/charge
nm Nanometer
NMR Nuclear magnetic resonance
ns Nanosecond(s)
ppb Parts per billion
ppm Parts per million
s Singlet
t Triplet
TLC Thin layer chromatography
v/v Volume/volume Materials and Methods All the metal salts used for the titrations provided herein were perchlorates with formula, $M(ClO_4)_2 \cdot xH_2O$. All the solvents used were of analytical grade and were purified and dried by routine procedures immediately before use. $^1H$ and $^{13}C$ NMR spectra were recorded on a Varian Mercury NMR spectrometer working at 400 MHz. The mass spectra were recorded on Q-TOF micromass (YA-105) spectrometer using electronspray ionization method. Steady state fluorescence spectra were measured on Perkin-Elmer LS55. The absorption spectra were measured on Shimadzu UV2101 PC. The elemental analyses were performed on ThermoQuest microanalysis. FT IR spectra were measured on Perkin-Elmer spectrometer using KBr pellets. AFM studies were performed in multimode Veeco Dimensions 3100 SPM with Nanoscope IV controller instrument. Scanning electron micrographs (SEM) were measured on a Hitachi S3400 cold-cathode Field Emission Scanning Electron Microscope.

Steady state fluorescence emission spectra were measured on Perkin-Elmer LS55 by exciting the solutions at 320 nm and measuring the emission spectra in 330-480 nm range. In the fluorescence studies performed in $CH_3OH$ solution, a 50 μl of $CHCl_3$ solution of calix[4]arene (VIII) (i.e., the 3 mL solution contains 2.950 mL of $CH_3OH$ and 0.050 mL of $CHCl_3$) was always used. All the measurements were made using 1 cm quartz cell and a final calix[4]arene (VIII) concentration of 10 μM was maintained. During the titration, the concentration of metal perchlorate was varied accordingly in order to result in the requisite mol ratios of metal ion to calix[4]arene (VIII), and the total volume of the solution was maintained constant at 3 mL in each case by adding appropriate solvent or solvent mixtures. The same solutions were used for absorption studies.

All the absorption studies were carried out in Shimadzu UV-2101 PC. 10 μM solution of IX was used for initial absorption studies. Absorption spectra were also recorded at higher ligand concentration, $3.64 \times 10^{-4}$ M and varied the $Cu^{2+}$ concentration. Proper controls were used as reference while recording the spectra.

Synthetic and analytical methods were carried out as described in R. Joseph, B. Ramanujam, H. Pal, and C. P. Rao, Tetrahedron Letters (2008) 49, 6257-61 and R. Joseph, B. Ramanujam, A. Acharya, C. P. Rao, Tetrahedron Letters (2009) 50, 2735-39, the entire contents of which are herein incorporated by reference for any and all purposes.

Example 1

Synthesis of bis-{N-(2,2'-dipyridylamide)} Derivative of calix[4]arene (VIII)

Scheme 2

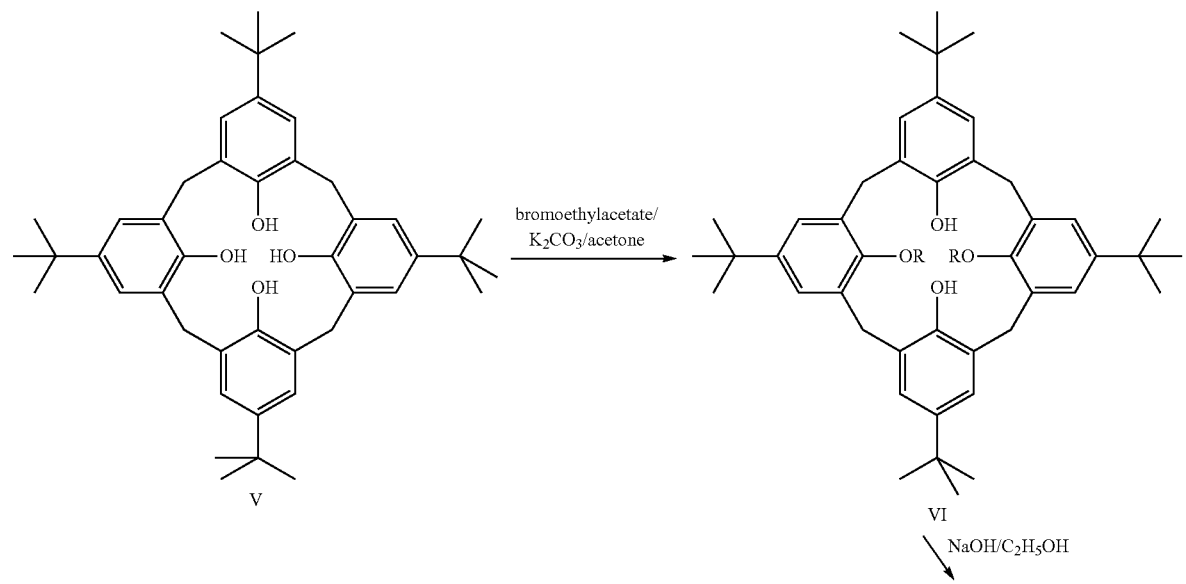

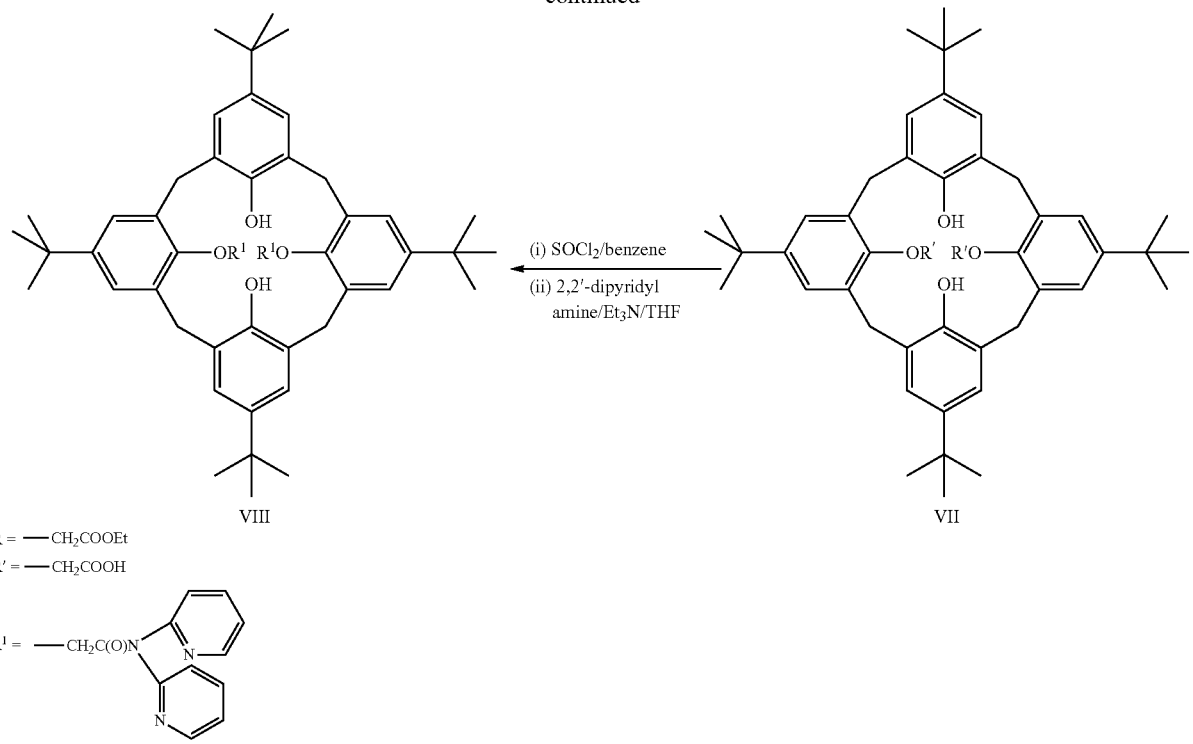

R = —CH₂COOEt
R' = —CH₂COOH
R¹ = —CH₂C(O)N(dipyridyl)

Synthesis and Characterization of VI:

A mixture of V (10 g, 15.4 mmol), potassium carbonate (4.26 g, 30.8 mmol), and ethyl bromoacetate (5.14 mL, 30.8 mmol) were taken in dry acetone (1.6 L) and was stirred and heated at reflux for 15 h under nitrogen atmosphere. The cooled reaction mixture was filtered through a bed of celite and the filtrate and dichloromethane washings of the celite were combined and concentrated to dryness. Recrystallization of the residue from ethanol yielded the diester. Yield (9.86 g, 78%). 1H NMR (CDCl₃, δ ppm): 0.98 (s, 18H, C(CH₃)₃), 1.26 (s, 18H each, C(CH₃)₃), 1.34 (t, 6H, CH₂—CH₃, J=7.02 Hz), 3.32 (d, 4H, Ar—CH₂—Ar, J=13.4 Hz), 4.30 (q, 4H, CH₂—CH₃), 4.45 (d, 4H, Ar—CH₂—Ar, J=13.2 Hz), 4.73 (s, 4H, OCH₂CO), 6.82 (s, 4H, Ar—H), 7.02 (s, 4H, Ar—H), 7.06 (s, 2H, OH).

Synthesis and Characterization of VII:

A mixture of the diester, VI, (10 g, 12.2 mmol) and 15% aq. sodium hydroxide (32 mL) in ethanol (500 ml) were stirred and heated under reflux for 24 h and the reaction mixture was evaporated under reduced pressure to yield white residue. The residue was diluted (suspension) with cold water (500 ml) and hydrochloric acid (3 N) was added with vigorous mixing until pH 1 was reached. The solid was filtered, dried in air and was further dissolved in chloroform. The solution was washed with hydrochloric acid (3 N) and brine, dried and concentrated to afford the diacid product, VII. VII was recrystallised from aq. acetone (acetone:water, 7:3 v/v). Yield (7.92 g, 85%). 1H NMR (CDCl₃, δ ppm): 1.10 (s, 18H each, C(CH₃)₃), 1.30 (s, 18H each, C(CH₃)₃), 3.46 (d, 4H, Ar—CH₂—Ar, J=13.74 Hz), 4.13 (d, 4H, Ar—CH₂—Ar, J=13.44 Hz), 4.70 (s, 4H, OCH₂CO), 6.99 (s, 4H, Ar—H), 7.07 (s, 4H, Ar—H).

Synthesis and Characterization of VIII:

To dry benzene (100 mL), p-tert-butylcalix[4]arene diacid, VII, (4.0 g) and SOCl₂ (6 mL) were refluxed under nitrogen atmosphere for 4 h. The solvent and residual SOCl₂ were removed under reduced pressure, and this yielded diacid chloride, as off white solid and was used in situ for the preparation of the receptor molecules VIII.

A suspension of 2,2'-dipyridylamine (0.52 g, 3 mmol) and Et₃N (0.9 mL, 6 mmol) was stirred in dry THF (20 mL) under argon atmosphere. Diacid chloride (1 g, 1.25 mmol) in dry THF (10 mL) was added drop wise to this reaction mixture. Immediately a white precipitate was formed and stirring was continued for 15 h at room temperature. After filtration, the filtrate was concentrated to dryness. A yellow solid was obtained which was extracted with CHCl₃, washed with water (2×6 ml) and then with brine (1×6 ml), and the organic layer was dried with MgSO₄. Filtrate was concentrated to dryness and re-crystallized from EtOH/CHCl₃ to get the final product as light yellow solid.

The purity of compound VIII was checked by TLC using CHCl₃/CH₃OH in 9.3:0.7 v/v ratio to result in one single spot with $R_f$=0.37. Mp 165-170° C. (decomposes).

Yield (40%, 0.58 g).

Anal. Calcd for $C_{68}H_{74}N_6O_6$ (1071.63): C, 76.22; H, 6.96; N, 7.84. Found: C, 76.32; H, 7.43; N, 7.57.

FTIR: (KBr, cm⁻¹): 1653 ($\nu_{C=O}$), 3343 ($\nu_{OH}$).

¹H NMR: (CDCl₃, 400 MHz δ ppm): 0.95 (s, 18H, C(CH₃)₃), 1.23 (s, 18H, C(CH₃)₃), 3.21 (d, 4H, Ar—CH₂—Ar, J=13.14 Hz), 4.37 (d, 4H, Ar—CH₂—Ar, J=13.14 Hz), 4.79 (s, 4H, —OCH₂CO—), 6.76 (s, 4H, Ar—H), 6.96 (s, 4H, Ar—H), 7.13 (t, 4H, Py-H, J=4.88 Hz), 7.33 (s, 2H, —OH), 7.61 (d, 4H, Py-H, J=7.94 Hz), 7.74 (t, 4H, Py-H, J=6.10 Hz), 8.42 (d, 4H, Py-H, J=5.81 Hz).

¹³C NMR: (CDCl₃, ~100 MHz δ ppm): 31.16, 31.79 (C(CH₃)₃), 31.88 (Ar—CH₂—Ar), 33.88, 34.98 (C(CH₃)₃), 74.81 (OCH₂CO), 122.29, 125.05, 125.66, 128.07, 132.87, 138.52, 141.24, 146.93, 148.95, 150.54, 151.17, 153.77 (py and calix-Ar—C), 169.23 (C=O).

m/z (ES-MS) 1071.72 ([M]⁺ 100%), 1072.72 ([M+H]⁺ 45%).

Example 2

Crystallization of bis-{N-(2,2'-dipyridylamide)} Derivative of calix[4]arene (VIII)

Single crystals of VIII obtained from slow evaporation of an acetonitrile solution illustrated the ORTEP diagram, as shown in FIG. 1. The crystal structure clearly shows the presence of a cone conformation of calix[4]arene and is in conformity with the result obtained based on NMR analysis. Based on the crystal structure, calix[4]arene, can be visualized as having at least two binding cores: one with the pyridyl environment having four nitrogens ($N_4$) and the other with the lower rim plus amide oxygens ($O_4$ or $O_6$) (FIG. 1). Such binding cores were formed owing to the extended conformation exhibited by both the arms. Bent arms were generally found for pendants possessing CO—NH groups by forming a hydrogen bond between NH and the phenolic OH.

Below are the metric parameters obtained from the single crystal X-ray structure of VIII.

Crystallographic data: $C_{68}H_{74}N_6O_6$, $CH_3CN$, M=1109.37, Triclinic, P-1 (P—onebar, No. 2), a=11.0956(1) Å, b=12.860(2) Å, c=22.387(5) Å, α=82.67(2)°, β=82.05(1)° γ=86.09(1)°, V=3133.7(9) Å$^3$, Z=2, $\rho_{calc}$=1.176 g cm$^{-3}$, μ=0.076 mm$^{-1}$, F(000)=1182, crystal size=0.28×0.30×0.35 mm$^3$, Temperature=150 K, Radiation MoKα=0.71073 Å, θ=3.0, 25.0°, range of h, k, l collected=−13 to 13; −15 to 15; −26 to 26, total data=32658, R(int)=0.061, Observed data [I>2.0 sigma(I)]=3188, Number of reflections used=11019, Number of parameters refined=760, R=0.1186, wR2=0.3701, S=0.94, w=1/[\s^2^(Fo^2^)+(0.2000P)^2^] where P=(Fo^2^+2Fc^2^)/3, Max. and Av. Shift/Error=0.08, 0.00, Min. and Max. Resd. Dens. [e/Ang^3]=−0.45, 1.03.

TABLE 1

Selected bond distances

| | | | |
|---|---|---|---|
| O1—C11 | 1.234(7) | C4—C5 | 1.302(8) |
| O2—C12 | 1.460(7) | C6—C7 | 1.276(13) |
| O2—C13 | 1.373(6) | C7—C8 | 1.382(19) |
| O3—C33 | 1.367(7) | C8—C9 | 1.37(3) |
| O4—C55 | 1.377(7) | C9—C10 | 1.30(4) |
| O5—C45 | 1.397(6) | C11—C12 | 1.499(9) |
| O5—C68 | 1.414(6) | C13—C14 | 1.374(8) |
| O6—C67 | 1.212(7) | C13—C22 | 1.427(8) |
| O3—H3 | 0.8200 | C14—C56 | 1.529(8) |
| O4—H4 | 0.8200 | C14—C15 | 1.404(9) |
| N1—C6 | 1.426(8) | C15—C16 | 1.392(9) |
| N1—C5 | 1.437(8) | C16—C17 | 1.528(9) |
| N1—C11 | 1.376(8) | C16—C21 | 1.398(9) |
| N2—C1 | 1.380(9) | C17—C19 | 1.481(12) |
| N2—C5 | 1.405(9) | C17—C20 | 1.526(11) |
| N3—C10 | 1.377(19) | C17—C18 | 1.487(14) |
| N3—C6 | 1.301(13) | C21—C22 | 1.369(9) |
| N4—C67 | 1.386(8) | C22—C23 | 1.525(9) |
| N4—C57 | 1.435(8) | C23—C24 | 1.514(9) |
| N4—C66 | 1.415(7) | C24—C33 | 1.390(8) |
| N5—C61 | 1.396(17) | C24—C25 | 1.378(9) |
| N5—C57 | 1.334(12) | C25—C26 | 1.392(9) |
| N6—C66 | 1.385(9) | C26—C31 | 1.398(9) |
| N6—C62 | 1.375(9) | C26—C27 | 1.525(9) |
| N111—C222 | 1.282(18) | C27—C28 | 1.481(13) |
| C1—C2 | 1.388(9) | C27—C30 | 1.482(11) |
| C2—C3 | 1.364(9) | C27—C29 | 1.559(12) |
| C3—C4 | 1.350(8) | C31—C32 | 1.377(9) |
| C32—C34 | 1.537(8) | C59—C60 | 1.28(3) |
| C32—C33 | 1.406(8) | C60—C61 | 1.36(2) |
| C34—C35 | 1.509(8) | C62—C63 | 1.359(9) |
| C35—C36 | 1.389(6) | C63—C64 | 1.372(9) |
| C35—C45 | 1.382(8) | C64—C65 | 1.312(8) |
| C36—C37 | 1.395(8) | C65—C66 | 1.324(8) |
| C37—C42 | 1.399(9) | C67—C68 | 1.489(8) |

TABLE 1-continued

Selected bond distances

| | | | |
|---|---|---|---|
| C37—C38 | 1.509(8) | C49—C50 | 1.591(12) |
| C38—C40 | 1.474(11) | C53—C54 | 1.386(9) |
| C38—C39 | 1.512(11) | C54—C56 | 1.502(8) |
| C38—C41 | 1.548(11) | C54—C55 | 1.390(8) |
| C42—C43 | 1.394(9) | C57—C58 | 1.236(13) |
| C43—C44 | 1.513(8) | C58—C59 | 1.348(18) |
| C43—C45 | 1.408(8) | C48—C53 | 1.381(9) |
| C44—C46 | 1.500(8) | C48—C49 | 1.523(10) |
| C46—C55 | 1.427(8) | C49—C52 | 1.489(11) |
| C46—C47 | 1.385(9) | C49—C51 | 1.479(12) |
| C47—C48 | 1.394(9) | C111—C222 | 1.335(16) |

TABLE 2

Selected Bond Angles

| A...B...C | Angle(°) |
|---|---|
| C12-O2-C13 | 112.4(4) |
| C45-O5-C68 | 111.8(4) |
| C33-O3-H3 | 109.00 |
| C55-O4-H4 | 109.00 |
| C6-N1-C11 | 117.8(5) |
| C5-N1-C6 | 118.9(5) |
| C5-N1-C11 | 123.2(5) |
| C1-N2-C5 | 116.7(6) |
| C6-N3-C10 | 117.8(15) |
| C66-N4-C67 | 123.6(5) |
| C57-N4-C66 | 118.5(5) |
| C57-N4-C67 | 117.4(5) |
| C57-N5-C61 | 115.8(12) |
| C62-N6-C66 | 117.9(6) |
| N2-C1-C2 | 120.6(6) |
| C1-C2-C3 | 116.8(6) |
| C2-C3-C4 | 124.6(6) |
| C3-C4-C5 | 117.2(5) |
| N2-C5-C4 | 124.1(6) |
| N1-C5-N2 | 117.6(5) |
| N1-C5-C4 | 118.3(5) |
| N1-C6-N3 | 114.8(7) |
| N1-C6-C7 | 120.5(8) |
| N3-C6-C7 | 124.3(9) |
| C6-C7-C8 | 118.9(14) |
| C7-C8-C9 | 117.1(14) |
| C8-C9-C10 | 120.3(15) |
| N3-C10-C9 | 120(2) |
| C24-C25-C26 | 123.1(6) |
| C27-C26-C31 | 120.1(6) |
| C25-C26-C31 | 117.1(6) |
| C25-C26-C27 | 122.8(6) |
| C26-C27-C28 | 112.5(7) |
| C28-C27-C29 | 101.1(8) |
| C26-C27-C29 | 109.5(6) |
| C26-C27-C30 | 115.6(6) |
| C29-C27-C30 | 104.2(8) |
| C28-C27-C30 | 112.6(7) |
| C26-C31-C32 | 121.7(6) |
| C31-C32-C33 | 119.4(5) |
| C31-C32-C34 | 120.5(5) |
| C33-C32-C34 | 120.1(6) |
| O3-C33-C24 | 125.0(5) |
| C24-C33-C32 | 120.2(6) |
| O3-C33-C32 | 114.7(5) |
| C32-C34-C35 | 112.1(5) |
| C36-C35-C45 | 117.9(5) |
| O1-C11-C12 | 120.2(6) |
| O1-C11-N1 | 119.9(5) |
| N1-C11-C12 | 120.0(5) |
| O2-C12-C11 | 105.9(5) |
| O2-C13-C14 | 120.7(5) |
| C14-C13-C22 | 120.9(5) |
| O2-C13-C22 | 118.3(5) |
| C13-C14-C56 | 121.7(5) |
| C13-C14-C15 | 118.7(5) |
| C15-C14-C56 | 119.5(5) |

TABLE 2-continued

Selected Bond Angles

| A...B...C | Angle(°) |
|---|---|
| C14-C15-C16 | 122.4(6) |
| C15-C16-C17 | 120.6(6) |
| C17-C16-C21 | 123.1(6) |
| C15-C16-C21 | 116.3(6) |
| C16-C17-C20 | 110.7(6) |
| C18-C17-C19 | 109.7(8) |
| C16-C17-C19 | 112.8(6) |
| C19-C17-C20 | 104.1(7) |
| C18-C17-C20 | 110.4(8) |
| C16-C17-C18 | 109.1(6) |
| C16-C21-C22 | 124.0(6) |
| C21-C22-C23 | 121.0(6) |
| C13-C22-C21 | 117.5(6) |
| C13-C22-C23 | 121.5(5) |
| C22-C23-C24 | 111.3(5) |
| C25-C24-C33 | 118.5(6) |
| C23-C24-C25 | 119.5(5) |
| C23-C24-C33 | 122.0(6) |
| C40-C38-C41 | 106.2(7) |
| C37-C38-C39 | 112.4(6) |
| C37-C38-C40 | 110.1(6) |
| C37-C42-C43 | 123.5(6) |
| C44-C43-C45 | 120.6(5) |
| C42-C43-C45 | 117.5(5) |
| C42-C43-C44 | 121.7(5) |
| C43-C44-C46 | 111.6(5) |
| O5-C45-C35 | 120.0(5) |
| O5-C45-C43 | 118.5(5) |
| C35-C45-C43 | 121.5(5) |
| C44-C46-C47 | 120.7(5) |
| C47-C46-C55 | 116.4(5) |
| C44-C46-C55 | 122.8(5) |
| C46-C47-C48 | 124.0(6) |
| C47-C48-C49 | 121.2(6) |
| C47-C48-C53 | 116.2(6) |
| C49-C48-C53 | 122.6(6) |
| C48-C49-C50 | 107.1(6) |
| C50-C49-C51 | 107.1(7) |
| C50-C49-C52 | 102.0(6) |
| C51-C49-C52 | 115.0(8) |
| C48-C49-C51 | 111.2(7) |
| C48-C49-C52 | 113.6(6) |
| C48-C53-C54 | 124.2(6) |
| C55-C54-C56 | 121.4(5) |
| C53-C54-C55 | 117.2(5) |
| C53-C54-C56 | 121.4(5) |
| N3-C10-H10 | 120.00 |
| C9-C10-H10 | 120.00 |
| O2-C12-H12A | 111.00 |
| O2-C12-H12B | 111.00 |
| N111-C222-C111 | 176.1(13) |
| C64-C65-C66 | 117.3(5) |
| N6-C66-C65 | 122.4(5) |
| N4-C66-N6 | 118.7(5) |
| N4-C66-C65 | 118.9(5) |
| O6-C67-N4 | 120.6(6) |
| O6-C67-C68 | 119.8(6) |
| N4-C67-C68 | 119.6(5) |
| O5-C68-C67 | 107.2(5) |
| N2-C1-H1 | 120.00 |
| C34-C35-C45 | 121.6(4) |
| C34-C35-C36 | 120.3(5) |
| C35-C36-C37 | 124.2(5) |
| C38-C37-C42 | 120.4(5) |
| C36-C37-C38 | 124.2(5) |
| C36-C37-C42 | 115.4(5) |
| C37-C38-C41 | 110.9(6) |
| C39-C38-C40 | 110.7(7) |
| C39-C38-C41 | 106.3(6) |
| C46-C55-C54 | 122.0(5) |
| O4-C55-C46 | 122.0(5) |
| O4-C55-C54 | 116.0(5) |
| C14-C56-C54 | 111.0(5) |
| N5-C57-C58 | 121.4(8) |
| N4-C57-N5 | 116.2(7) |
| N4-C57-C58 | 121.4(8) |

TABLE 2-continued

Selected Bond Angles

| A...B...C | Angle(°) |
|---|---|
| C57-C58-C59 | 121.5(16) |
| C58-C59-C60 | 122(2) |
| C59-C60-C61 | 115.5(13) |
| N5-C61-C60 | 121.1(12) |
| N6-C62-C63 | 120.6(6) |
| C62-C63-C64 | 116.3(6) |
| C63-C64-C65 | 125.5(6) |

TABLE 3

Selected dihedral angles of the arm

| A...B...C...D | Dihedral angle | |
|---|---|---|
| | Arm1 | Arm2 |
| $C_{calix}$...O...$CH_2$...CO | 165.5 | 170.6 |
| O...$CH_2$...CO...N | 158.4 | 158.1 |
| $CH_2$...CO...N...$C_{py}$ | 12.0 | 176.6 |
| CO...N...$C_{py}$...$N_{py}$ | 148.3 | 93.1 |
| $CH_2$...CO...N...$C_{py}$' | 172.8 | 11.0 |
| CO...N...C'...$N_{py}$' | 104.2 | 145.1 |

TABLE 4

Selected Hydrogen Bonds (Angstrom, Deg)

| O3—H3...O2 | 0.8200 | 2.0100 | 2.787(6) | 157.00 |
|---|---|---|---|---|
| O4—H4...O5 | 0.8200 | 2.0400 | 2.791(6) | 152.00 |
| C1—H1...O4 | 0.9300 | 2.5900 | 3.410(8) | 148.00 |
| C2—H2...O6 | 0.9300 | 2.4800 | 3.131(8) | 128.00 |

Example 3

Figure 2:
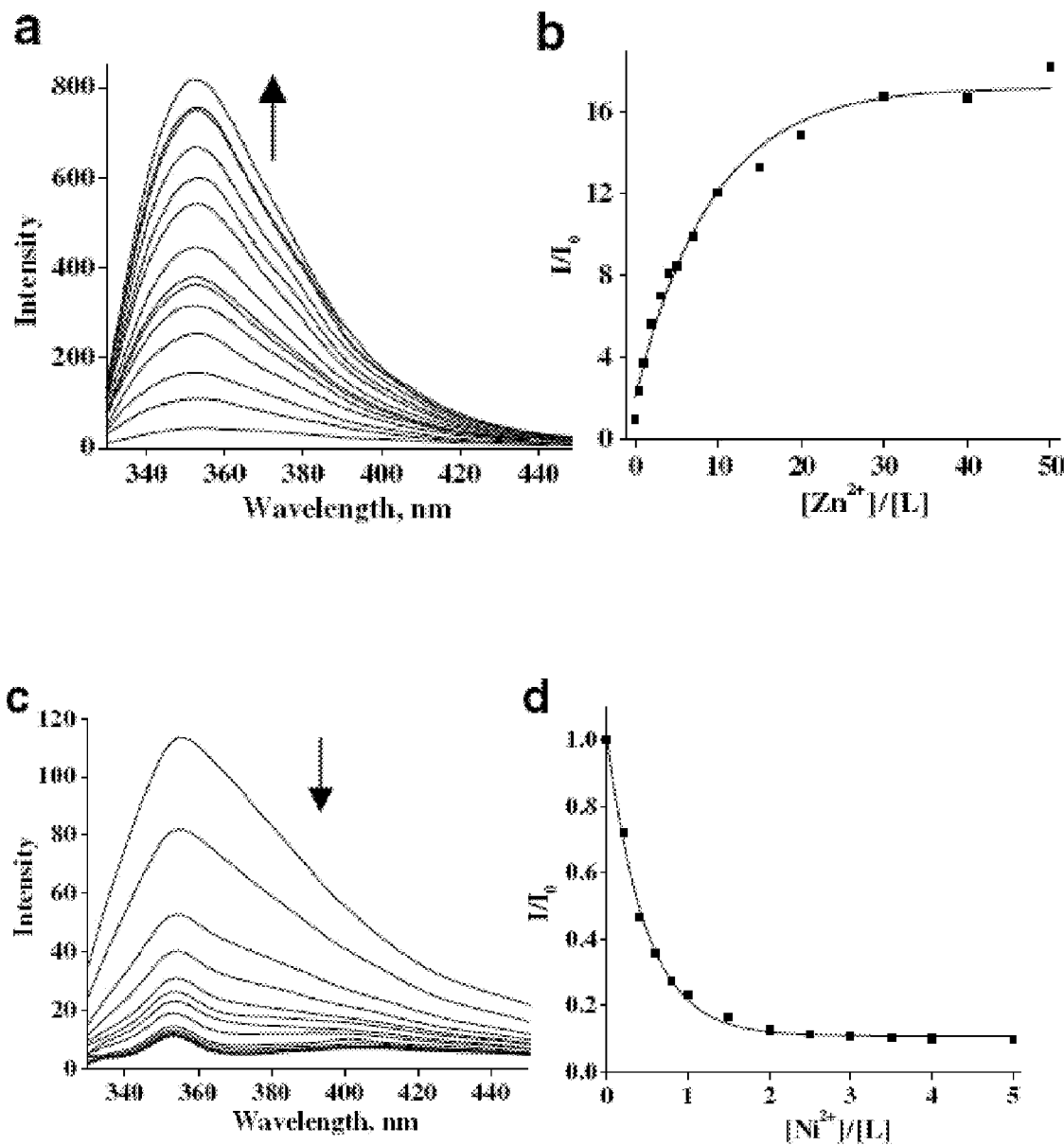
FIG. 2 depicts an illustrative embodiment of a fluorescence titration of bis-{N-(2,2'-dipyridylamide)} derivative of calix[4]arene (compound VIII) by $Zn^{2+}$ or $Ni^{2+}$: (a) spectral traces during the titration by $Zn^{2+}$; (b) plot of relative intensity $(I/I_o)$ versus $[Zn^{2+}]/[L]$ mol ratio; (c) spectral traces during the titration by $Ni^{2+}$; and (d) plot of relative intensity $(I/I_o)$ versus $[Ni^{2+}]/[L]$ mol ratio.

$Zn^{2+}$ and $Ni^{2+}$ Ion Binding with bis-{N-(2,2'-dipyridylamide)} Derivative of calix[4]arene (VIII) Studied by Fluorescence Spectroscopy The metal ion binding properties of calix[4]arene derivative VIII (shown as L in FIG. 2) were studied in methanol by fluorescence, absorption, and ESI MS.

During the titration of VIII by $M^{2+}$ (metal ion) using fluorescence spectroscopy, VIII showed progressive enhancement in the intensity upon addition of $Zn^{2+}$ (FIG. 2a) that saturated at ~10-20 equiv. This indicated an equilibrium driven reaction wherein the overall enhancement was found to be 16-18-fold at saturation (FIG. 2b) though it was at least eightfold at 2 mol equiv of $Zn^{2+}$. This is attributable to the reversal of the photoelectron transfer of the pyridyl-N lone pair upon $Zn^{2+}$ binding.

Similar titrations carried out with $Ni^{2+}$ exhibited fluorescence quenching (FIGS. 2c and 2d) owing to the paramagnetic nature of this ion. The complexed species formed were found to be 1:1 in both the cases. Based on the Benesi-Hildebrand equation, the association constants (Kass) were found to be 18,173±1726 and 238,930±13,060 $M^{-1}$, respectively, for $Zn^{2+}$ and $Ni^{2+}$ complexes. With respect to naphthalene, VIII was found to have a quantum yield of 0.0356. While this is increased by about three times in the presence of $Zn^{2+}$, it is decreased by three times in the presence of $Ni^{2+}$.

Figure 3:
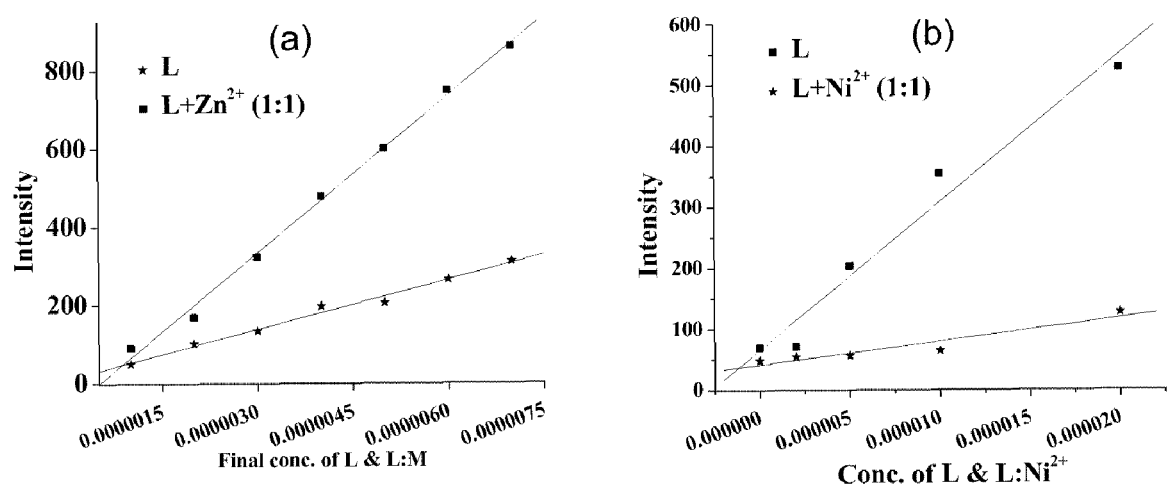
FIG. 3 depicts an illustrative embodiment of a dilution experiment (a) bis-{N-(2,2'-dipyridylamide)} derivative of calix[4]arene (compound VIII, shown as L in the figure) with $Zn^{2+}$; (b) L with $Ni^{2+}$ keeping the $M^{2+}$ to L ratio as 1:1 in order to identify the lowest detectable $M^{2+}$ concentration by L.
Figure 4:
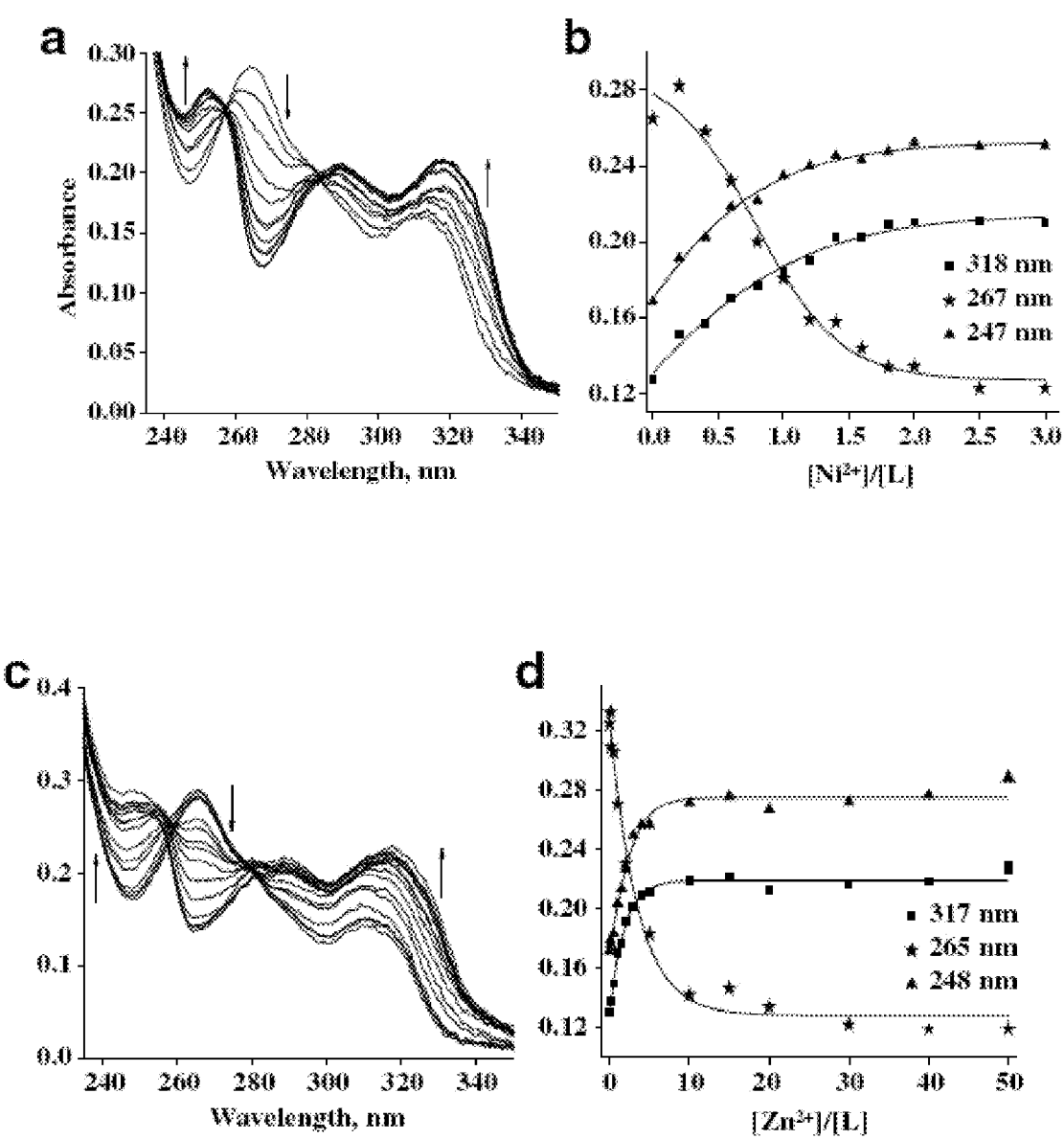
FIG. 4 depicts an illustrative embodiment of an absorption spectral data during the titration of bis-{N-(2,2'-dipyridylamide)} derivative of calix[4]arene (compound VIII, depicted as L in the figure) with $Ni^{2+}$ or $Zn^{2+}$: (a) spectral traces in case of $Ni^{2+}$; (b) absorbance versus $[Ni^{2+}]/[L]$ mol ratio; (c) spectral traces in case of $Zn^{2+}$; and (d) absorbance versus $[Zn^{2+}]/[L]$ mol ratio.

During the titration of calix[4]arene derivative VIII by $M^{2+}$ using fluorescence spectroscopy, calix[4]arene derivative VIII showed progressive enhancement in the intensity upon addition of $Zn^{2+}$. The minimum concentrations at which calix [4]arene derivative VIII (shown as L in FIG. 3) can detect $Zn^{2+}$ and $Ni^{2+}$ are 142 and 203 ppb, respectively (FIGS. 3a-b).

Example 4

$Zn^{2+}$ and $Ni^{2+}$ Ion Binding with bis-{N-(2,2'-dipyridylamide)} Derivative of calix[4]arene (VIII) Studied by ESI MS and Absorption Spectra In order to confirm the binding and stoichiometry of $Zn^{2+}$ or $Ni^{2+}$ with calix[4]arene derivative VIII, ESI MS spectra were measured in both the cases and the formation of 1:1 species was found at m/z 1160.8 and 1130 for $Zn^{2+}$ and $Ni^{2+}$, respectively. The isotopic peak pattern confirmed the presence of these metal ions.

The results were further supported by measuring the absorption spectra wherein isosbestic points were observed at 257 and 283 nm in case of $Ni^{2+}$, and 257 nm in the case of $Zn^{2+}$, indicating a transition between the complexed species and the free species (FIGS. 4a-d, calix[4]arene derivative VIII shown as L). Increase in the absorbance of 317-318 nm band is indicative of the interaction of $Ni^{2+}$ or $Zn^{2+}$ with nitrogens of pyridyl moieties present on both the arms.

Figure 5:
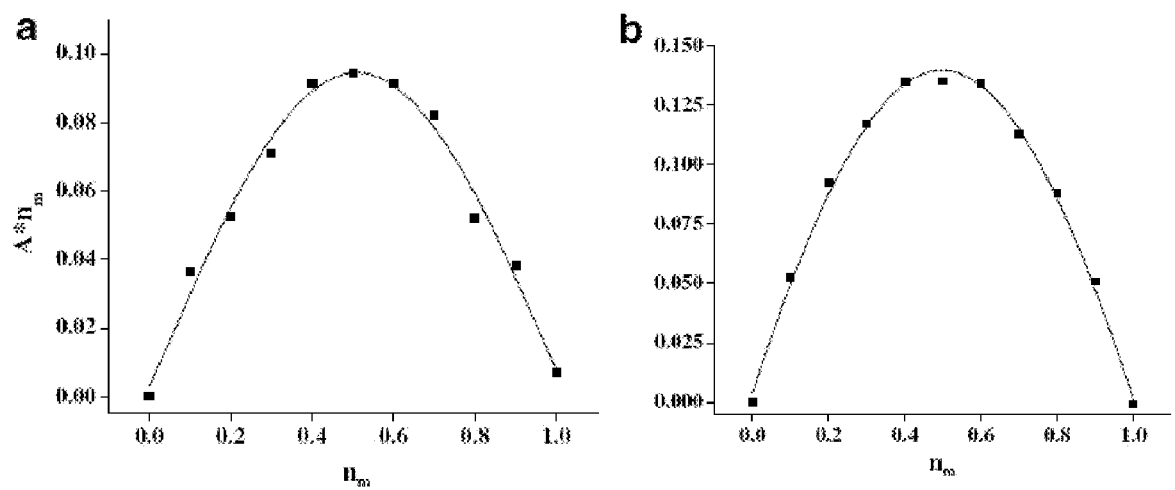
FIG. 5 depicts an illustrative embodiment of a Job plot of $n_m$, versus $A*n_m$, where $n_m$ is mol fraction of the metal ion added and A is absorbance: (a) $Ni^{2+}$ and (b) $Zn^{2+}$.

While the titration of $Zn^{2+}$ is equilibrium driven, that of the $Ni^{2+}$ is stoichiometric as already observed based on fluorescence studies, and the complexes formed were found to be 1:1 based on Job plots made using the absorption data (FIGS. 5a-b).

Example 5

Binding of Other Divalent Ions with calix[4]arene Derivative VIII

Figure 6:
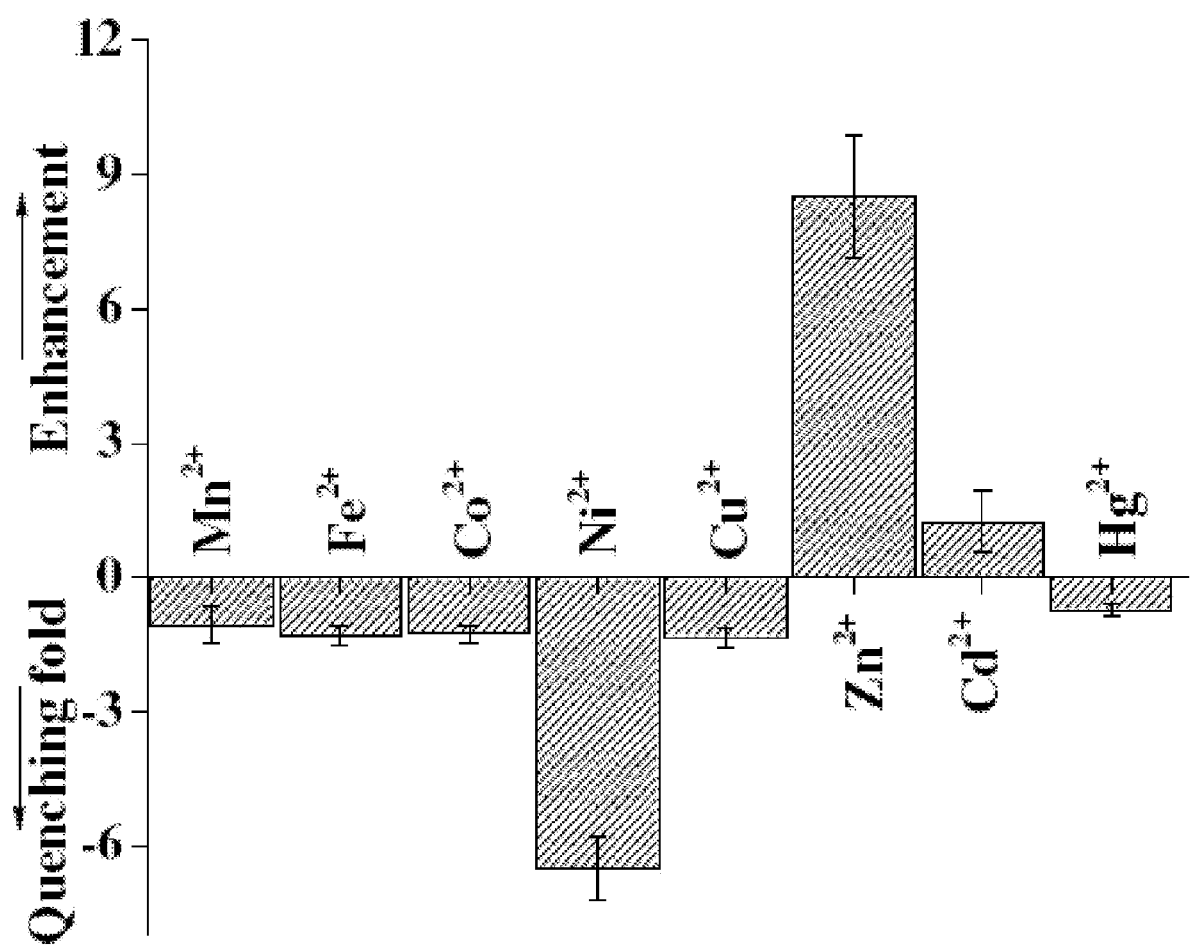
FIG. 6 depicts an illustrative embodiment of a histogram showing the number of times of quenching or enhancement in the relative fluorescence intensity $(I/I_o)$ in case of titration of bis-{N-(2,2'-dipyridylamide)} derivative of calix[4]arene (compound VIII, depicted as L in the figure) with $M^{2+}$ at 2 mol equiv of $M^{2+}$. The error bars were placed based on four different measurements.

Similar titrations of calix[4]arene derivative VIII carried out with other divalent ions, viz., $Mn^{2+}$, $Fe^{2+}$, $Co^{2+}$, $Cu^{2+}$ and $Hg^{2+}$, exhibited almost no fluorescence quenching, while those carried out with $Cd^{2+}$ exhibited marginal enhancement (FIG. 6). Thus, the steady-state fluorescence data obtained from the titration of calix[4]arene derivative VIII with $M^{2+}$ clearly suggests that calix[4]arene derivative VIII can detect $Zn^{2+}$ by switch-on and $Ni^{2+}$ by switch-off modes wherein the bipyridyl arms undergo appropriate conformational changes to accommodate either the $Zn^{2+}$ or the $Ni^{2+}$ ions.

Example 6

Titration Studies of $Zn^{2+}$ and $Ni^{2+}$ Ion Complexed with bis-{N-(2,2'-dipyridylamide)} Derivative of calix[4]arene (VIII)

Figure 7:
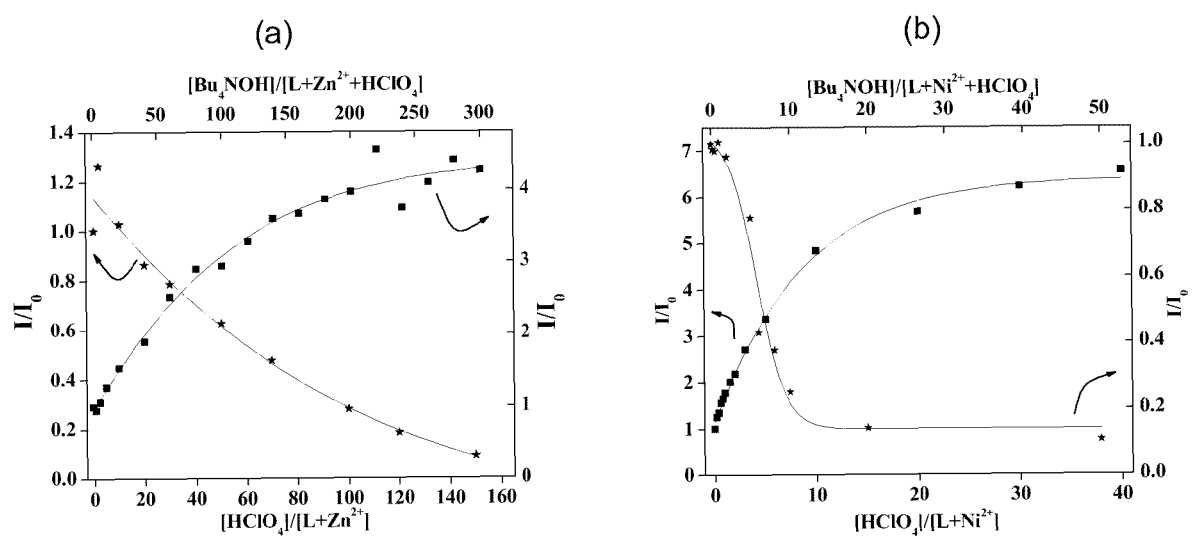
FIG. 7 depicts an illustrative embodiment of a titration of calix[4]arene derivative VIII (shown as L in FIG. 7) with: (a) L+$Zn^{2+}$ (1:20) with $HClO_4$ and L+$Zn^{2+}$+$HClO_4$ (1:20:150) with $Bu_4NOH$; and (b) L+$Ni^{2+}$ (1:2) with $HClO_4$ and L+$Ni^{2+}$+$HClO_4$ (1:2:10) with $Bu_4NOH$.

In order to establish the formation of the complex of calix [4]arene derivative VIII, reaction mixtures were titrated with perchloric acid followed by re-titration with $(n-C_4H_9)_4NOH$. FIG. 7 shows titration of (a) calix[4]arene derivative VIII (shown as L in FIG. 7)+$Zn^{2+}$ (1:20) with $HClO_4$ and L+$Zn^{2+}$+$HClO_4$ (1:20:150) with $Bu_4NOH$, and (b) L+$Ni^{2+}$ (1:2) with $HClO_4$ and L+$Ni^{2+}$+$HClO_4$ (1:2:10) with $Bu_4NOH$.

These studies showed switch on-off-on fluorescence behavior in the case of $Zn^{2+}$. The behavior was reverse in the case of the titration of calix[4]arene derivative VIII with $Ni^{2+}$.

Example 7

Fluorescence Life Time Studies of $Zn^{2+}$ and $Ni^{2+}$ Ion Complexed with bis-{N-(2,2'-dipyridylamide)} Derivative of calix[4]arene (VIII)

The formation of the complexed species by calix[4]arene derivative (VIII) was further studied by measuring the fluorescence life times of the complexes during the titration.

Time Resolved fluorescence Measurements: Time resolved data frequently contain more information than is available from the steady state data. Time-resolved fluorescence experiments were performed with a time-domain fluorescence spectrometer model 199 (Edinburgh Instruments, UK) which uses a gated hydrogen discharge lamp as the excitation source and EG & G ORTEC single photon-counting (SPC) data acquisition system, interfaced with an LSI-11/ 23 (Plessey, UK) computer. The observed fluorescence decay function F(t) was a convolution of the true fluorescence decay function G(t) [G(t)=$\Sigma_i B_i exp(-t/\tau_i)$, where $B_i$ is the pre-exponential factor and $\tau_i$ is the fluorescence lifetime for the $i^{th}$ component] and the instrument response function I(t) and was analysed by using an appropriate re-convolution program employing a non-linear iterative least-squares fit method. The mono- or multi-exponential behavior of the true decay associated with the observed fluorescence decay function and the corresponding computer fit was evaluated by minimum reduced $\chi^2$ value as well as by the distribution of the weighted residuals among the data channels and Durbin-Watson parameter.[12] The time resolution of the SPC unit, determined by Zimmermann's method[13] was found to be ca., 100 ps.

Figure 8:
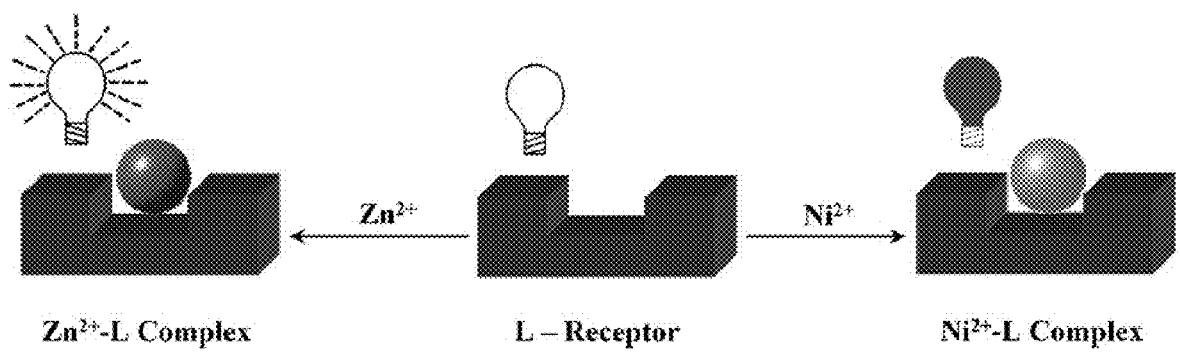
FIG. 8 depicts an illustrative embodiment of a switch-on and switch-off fluorescence behaviour of calix[4]arene derivative VIII (shown as L in FIG. 8) upon complexation with $Zn^{2+}$ and $Ni^{2+}$, respectively.

The fluorescence behavior of calix[4]arene derivative (VIII) in the presence of $Zn^{2+}$ or $Ni^{2+}$ is illustrated in FIG. 8 which shows the switch-on and switch-off fluorescence behavior of calix[4]arene derivative (VIII) upon complexation with $Zn^{2+}$ and $Ni^{2+}$, respectively.

Figure 9:
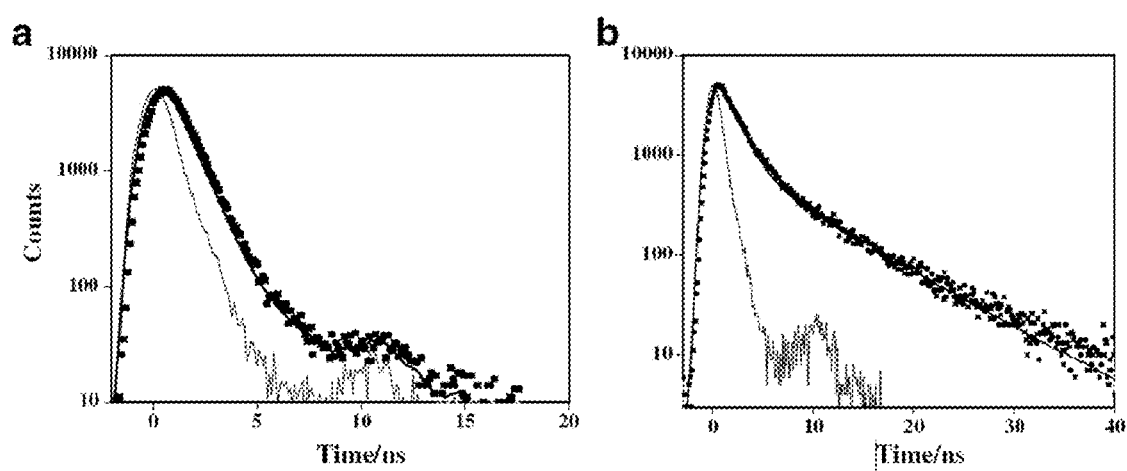
FIG. 9 depicts an illustrative embodiment of a fluorescence decay plot as a function of time during the titration of calix[4]arene derivative (VIII): (a) with $Zn^{2+}$ and (b) with $Ni^{2+}$. The trace with '-.-.-.' represent prompt for the lamp. The filled points represent the data. The line that passes through the points is the fit.

FIG. 9 illustrates a fluorescence decay plot as a function of time during the titration of calix[4]arene derivative (VIII): (a) with $Zn^{2+}$ and (b) with $Ni^{2+}$. The data of calix[4]arene derivative (VIII) alone fit with bi-exponential decay that is associated with two species having 0.33 ns (42%) and 2.12 ns (58%). When calix[4]arene derivative (VIII) is titrated against $Zn^{2+}$, the decay curve fits with a single species exclusively having 0.8 ns (100%), and when titrated with $Ni^{2+}$ it fits well with one major, viz., 1.76 ns (85%) and one minor, viz., 7.85 ns (15%) species. Thus the results of the life time measurements are in accordance with those of the steady state.

Example 8

Computational Calculations

For the computational calculations of the metal ion binding, the crystal structure of the calix[4]arene derivative (VIII) ("L" herein) was used. Since the number of atoms involved in the computations was too large, a model (L') was built by replacing the upper rim t-butyl groups with hydrogens. Thus, the L' has the same binding features as those of L. The L' was optimized in HF/3-21G followed by HF/6-31G before using for metal ion binding.

Frisch, M. J.; Trucks, G. W.; Schlegel, H. B.; Scuseria, G. E.; Robb, M. A.; Cheeseman, J. R.; Montgomery, J. A., Jr.; Vreven, T.; Kudin, K. N.; Burant, J. C.; Millam, J. M.; Iyengar, S. S. Tomasi, J.; Barone, V.; Mennucci, B.; Cossi, M.; Scalmani, G.; Rega, N.; Petersson, G. A.; Nakatsuji, H.; Hada, M.; Ehara, M.; Toyota, K.; Fukuda, R.; Hasegawa, J.; Ishida, M.; Nakajima, T.; Honda, Y.; Kitao, O.; Nakai, H.;

Klene, M.; Li, X.; Knox, J. E.; Hratchian, H. P.; Cross, J. B.; Adamo, C.; Jaramillo, J.; Gomperts, R.; Stratmann, R. E.; Yazyev, O.; Austin, A. J.; Cammi, R.; Pomelli, C.; Ochterski, J. W.; Ayala, P. Y.; Morokuma, K.; Voth, G. A.; Salvador, P.; Dannenberg, J. J.; Zakrzewski, V. G.; Dapprich, S.; Daniels, A. D.; Strain, M. C.; Farkas, O.; Malick, D. K.; Rabuck, A. D.; Raghavachari, K.; Foresman, J. B.; Ortiz, J. V.; Cui, Q.; Baboul, A. G.; Clifford, S.; Cioslowski, J.; Stefanov, B. B.; Liu, G.; Liashenko, A.; Piskorz, P.; Komaromi, I.; Martin, R. L.; Fox, D. J.; Keith, T.; Al-Laham, M. A.; Peng, C. Y.; Nanayakkara, A.; Challacombe, M.; Gill, P. M. W.; Johnson, B. W.; Wong, W.; Gonzalez, C. and Pople, J. A. *Gaussian* 03, Revision B.05; Gaussian, Inc.: Pittsburgh, Pa., 2003.

Figure 10:
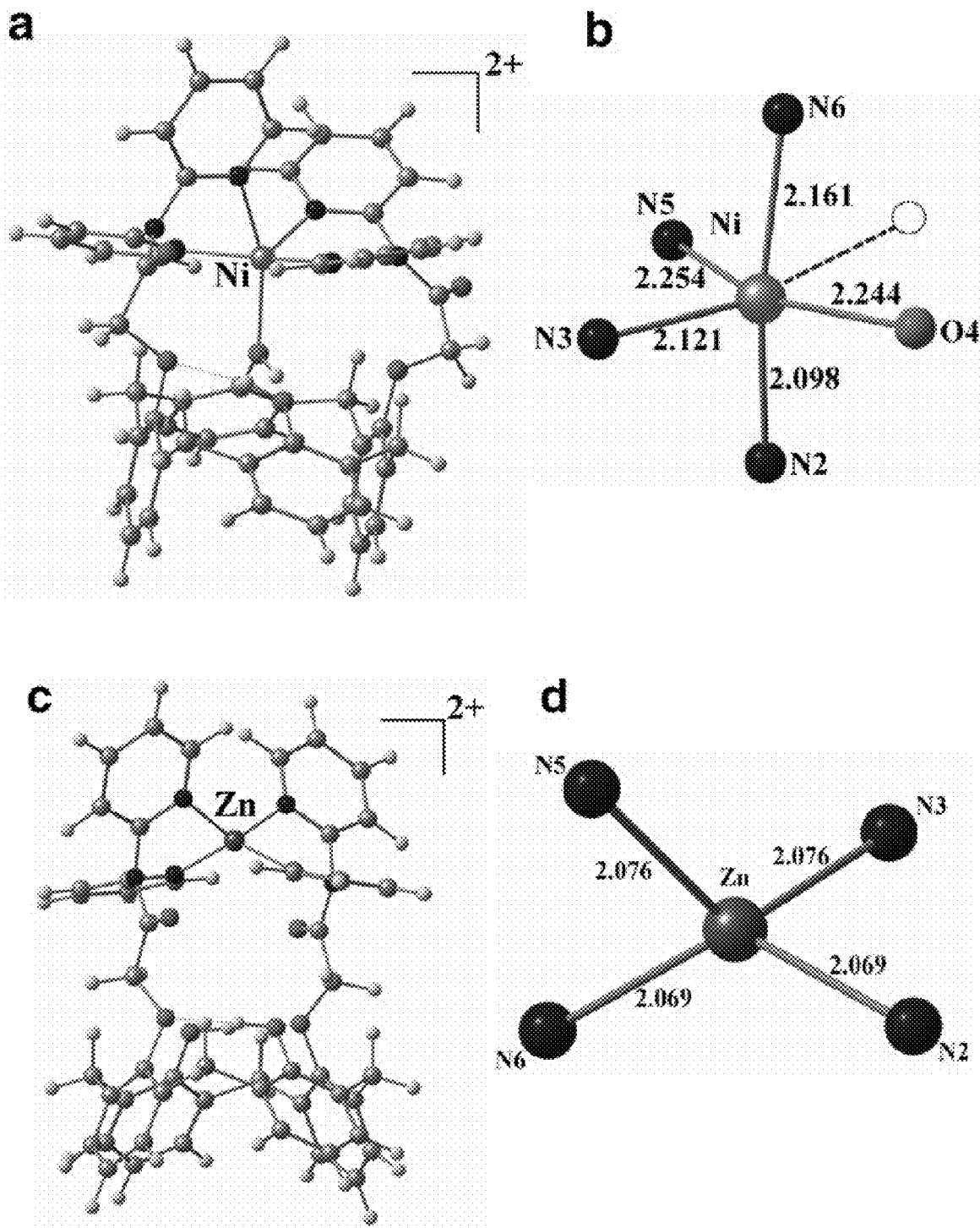
FIG. 10 depicts an illustrative embodiment of a UHF/6-31G optimized structures of (a) $Ni^{2+}$-L' complex; (b) coordination sphere of $Ni^{2+}$ in (a), the open circle shown in the coordination sphere refers to the vacant site; (c) $Zn^{2+}$-L' complex and (d) coordination sphere of $Zn^{2+}$ in (c). Metal to ligand distances in Å are shown on the bonds. The bond angles at the $Ni^{2+}$ coordination site were found to be: N2 ... Ni ... N3=82.7; N2 ... Ni ... N5=105.1; N2 ... Ni ... N6=160.2; N2 ... Ni ... O4=88.6; N3 ... Ni ... N5=90.9; N3 ... Ni ... N6=85.0; N3 ... Ni ... O4=114.5; N5 ... Ni ... N6=90.4; N5 ... Ni ... O4=154.6 and N6 ... Ni ... O4=96.1 Å. The bond angles at the $Zn^{2+}$ coordination site were found to be: N2 ... Zn ... N3=95.3; N2 ... Zn ... N5=106.3; N2 ... Zn ... N6=133.7; N3 ... Zn ... N5=123.3; N3 ... Zn ... N6=106.3 and N5 ... Zn ... N6=95.3 Å.

The initial geometry for the computations of the metal-bound species was obtained by placing $Ni^{2+}$ or $Zn^{2+}$ at a non-interacting position well above the pyridyl core of the optimized L'. The computational calculations carried out in the case of the $[Ni-L']^{2+}$ complex exhibited $Ni^{2+}$ a distorted octahedral geometry (FIG. 10a) with one of the ligating sites being vacant and bound through all four pyridyl nitrogens plus one lower rim phenolic-OH (FIG. 10b). Similar optimization yielded $Zn^{2+}$ in a distorted tetrahedral geometry (FIG. 10c) wherein the metal ion is bound through all four pyridyl nitrogens in the $[Zn-L']^{2+}$ complex (FIG. 10d). The complexation is a result of metal ion-induced conformational changes

TABLE 5

Cartesian coordinates of HF/6-31G optimized L'

| Z | X | Y | z | Z | x | y | z |
|---|---|---|---|---|---|---|---|
| 1 | 9.241379 | −0.758849 | −1.363741 | 6 | −1.81569 | −1.30636 | 2.667719 |
| 6 | 8.221693 | −0.718828 | −1.038731 | 6 | −3.184143 | −3.226297 | −3.574451 |
| 1 | 7.819886 | −2.804495 | −1.319975 | 6 | −2.599206 | −2.124327 | −2.964685 |
| 1 | 8.215791 | 1.385128 | −0.616344 | 1 | −1.571275 | −0.055277 | 1.147646 |
| 6 | 7.423111 | −1.856368 | −1.014078 | 1 | −2.989382 | 7.120932 | 2.461394 |
| 6 | 7.657745 | 0.471651 | −0.626732 | 6 | −3.817847 | −2.088205 | 3.710996 |
| 6 | 6.109812 | −1.773626 | −0.589881 | 1 | −1.288365 | 8.699061 | 1.552009 |
| 7 | 6.390485 | 0.556133 | −0.223619 | 1 | −4.181299 | −3.145765 | −3.964617 |
| 1 | 5.479562 | −2.632563 | −0.582129 | 6 | −3.189509 | −1.16922 | 2.877097 |
| 6 | 5.626123 | −0.52368 | −0.204163 | 6 | −2.326938 | 6.816855 | 1.674586 |
| 1 | 5.267212 | 0.127392 | 2.738609 | 6 | −1.381272 | 7.701968 | 1.172477 |
| 1 | 2.00999 | −0.787032 | 1.54971 | 8 | −2.882723 | 2.809335 | 1.004548 |
| 1 | 1.514097 | 0.173094 | 0.186808 | 1 | −4.872488 | −1.99344 | 3.89094 |
| 7 | 4.305154 | −0.318398 | 0.283899 | 1 | −2.648678 | −0.011119 | −2.835202 |
| 1 | 0.88409 | −6.080685 | −1.019082 | 6 | −3.359608 | −0.815979 | −2.808993 |
| 1 | 4.813851 | 2.152801 | 4.10087 | 1 | −3.134909 | 4.842987 | 1.561329 |
| 6 | 4.64928 | 0.918757 | 2.367829 | 6 | −2.426609 | 5.532658 | 1.169694 |
| 1 | 1.342554 | −4.337358 | −2.610761 | 8 | −2.595347 | 0.414771 | −0.176237 |
| 6 | 0.794632 | −5.754252 | 1.087528 | 6 | −4.220427 | −0.782275 | −1.546942 |
| 6 | 0.851003 | −5.348122 | −0.235546 | 6 | −3.812063 | −0.260133 | −0.318944 |
| 6 | 1.889986 | −0.790817 | 0.480701 | 1 | −4.016039 | −0.692311 | −3.663461 |
| 6 | 4.392894 | 2.051397 | 3.119963 | 6 | −3.995012 | −0.054001 | 2.219112 |
| 6 | 4.087523 | 0.833968 | 1.102613 | 1 | −3.405901 | 0.844438 | 2.134044 |
| 1 | 0.606133 | −5.125271 | 3.109301 | 6 | −0.559755 | 7.248864 | 0.160628 |
| 6 | 0.697023 | −4.807921 | 2.088279 | 6 | −4.54379 | −0.450638 | 0.855413 |
| 6 | 0.864991 | −4.000751 | −0.567152 | 1 | −5.829813 | −1.773042 | −2.531637 |
| 6 | 3.231093 | −1.054576 | −0.181216 | 6 | −5.475716 | −1.388213 | −1.594627 |
| 1 | 0.88934 | −2.879241 | 3.848615 | 6 | −2.234017 | 2.796827 | −0.029963 |
| 6 | 0.829277 | −3.580671 | −2.030033 | 6 | −1.548729 | 5.164949 | 0.146093 |
| 1 | 1.38043 | −2.665582 | −2.163306 | 1 | 0.192007 | 7.873187 | −0.276997 |
| 7 | 3.313483 | 1.780925 | 0.604852 | 6 | −5.777784 | −1.079818 | 0.758394 |
| 6 | 0.685007 | −3.440980 | 1.806242 | 6 | −6.256192 | −1.525063 | −0.462763 |
| 6 | 0.846667 | −3.065626 | 0.471961 | 1 | −6.364554 | −1.220174 | 1.645885 |
| 6 | 3.574457 | 3.045459 | 2.597689 | 7 | −0.650715 | 6.014939 | −0.330617 |
| 1 | −0.684059 | −5.457261 | −3.262105 | 1 | −4.833174 | 0.181207 | 2.864154 |
| 8 | 0.895899 | −1.723070 | 0.072724 | 6 | −2.244343 | 1.569286 | −0.927436 |
| 6 | 3.042733 | 2.865607 | 1.333975 | 7 | −1.544371 | 3.896200 | −0.497401 |
| 6 | 0.400507 | −2.485332 | 2.964212 | 1 | −1.292833 | 1.363485 | −1.376038 |
| 1 | 3.346616 | 3.928007 | 3.159902 | 1 | −2.970480 | 1.757201 | −1.707742 |
| 1 | 0.79893 | −1.504431 | 2.789655 | 6 | −0.612555 | 3.736042 | −1.579401 |
| 8 | 3.353727 | −1.900278 | −1.053258 | 7 | 0.538236 | 3.158184 | −1.281912 |
| 1 | −1.196816 | −4.019523 | 4.56269 | 1 | −1.876159 | 4.619892 | −3.054216 |
| 1 | 2.382755 | 3.578295 | 0.886806 | 6 | −0.935201 | 4.147721 | −2.859872 |
| 6 | −1.215523 | −4.527818 | −3.17759 | 6 | 1.440352 | 2.958843 | −2.243427 |
| 6 | −0.588289 | −3.443609 | −2.573428 | 1 | 2.348804 | 2.481849 | −1.941085 |
| 6 | −1.748262 | −3.228458 | 4.09033 | 6 | −0.000776 | 3.947725 | −3.864106 |
| 6 | −1.086431 | −2.341087 | 3.252761 | 6 | 1.209303 | 3.344280 | −3.553729 |
| 1 | −0.143055 | −1.257284 | −1.204495 | 1 | −0.214689 | 4.255362 | −4.868702 |
| 6 | −2.500321 | −4.426144 | −3.683869 | 1 | 1.951141 | 3.169955 | −4.306247 |
| 6 | −1.295332 | −2.242454 | −2.485686 | 1 | −2.962548 | −5.270421 | −4.158042 |
| 8 | −0.718718 | −1.108867 | −1.962764 | 1 | −7.218666 | −1.995065 | −0.526277 |
| 6 | −3.108986 | −3.107838 | 4.32311 | 1 | 0.801469 | −6.798902 | 1.332706 |
| 8 | −1.107405 | −0.402668 | 1.914674 | 1 | −3.609556 | −3.799068 | 4.973463 | brought in the pendant arms of L so that the core possessing the ligating atoms is well poised for binding.

TABLE 6

Cartesian coordinates of UHF/3-21G optimized [Ni-L']$^{2+}$

| Z | x | y | z |
|---|---|---|---|
| 1 | 5.711413 | −0.224032 | −3.608776 |
| 6 | 4.950743 | −0.798049 | −3.121682 |
| 1 | 5.371585 | −2.622878 | −4.161213 |
| 1 | 4.243925 | 0.821084 | −1.914604 |
| 6 | 4.758392 | −2.138947 | −3.428112 |
| 6 | 4.136238 | −0.209373 | −2.174703 |
| 6 | 3.761511 | −2.848599 | −2.775069 |
| 7 | 3.171219 | −0.894822 | −1.549728 |
| 1 | 3.572564 | −3.878071 | −2.993461 |
| 6 | 2.993593 | −2.177987 | −1.845802 |
| 1 | 2.503868 | −5.114201 | 0.163538 |
| 1 | −1.009250 | −4.263719 | −1.723053 |
| 1 | −0.142377 | −4.316770 | −0.189063 |
| 7 | 1.946366 | −2.816791 | −1.110523 |
| 1 | −5.593182 | −2.885998 | −0.278560 |
| 1 | 3.046869 | −5.302833 | 2.579876 |
| 6 | 2.503455 | −4.251250 | 0.797040 |
| 1 | −4.234201 | −3.145288 | −2.486589 |
| 6 | −4.577160 | −3.028137 | 1.590886 |
| 6 | −4.641234 | −2.877967 | 0.215355 |
| 6 | −0.397246 | −3.702565 | −1.036433 |
| 6 | 2.815930 | −4.349076 | 2.149553 |
| 6 | 2.212763 | −3.008435 | 0.275274 |
| 1 | −3.320896 | −3.046912 | 3.313587 |
| 6 | −3.356729 | −2.965046 | 2.244745 |
| 6 | −3.485754 | −2.694245 | −0.536701 |
| 6 | 0.789036 | −3.166049 | −1.794093 |
| 1 | −0.704206 | −3.525268 | 2.878750 |
| 6 | −3.575771 | −2.417437 | −2.031117 |
| 1 | −2.610139 | −2.550421 | −2.504253 |
| 7 | 2.241062 | −1.897449 | 1.026233 |
| 6 | −2.179709 | −2.784036 | 1.528786 |
| 6 | −2.275303 | −2.691480 | 0.146280 |
| 6 | 2.839866 | −3.201438 | 2.924407 |
| 1 | −5.879439 | −1.760120 | −3.290827 |
| 8 | −1.084896 | −2.512089 | −0.600573 |
| 6 | 2.546615 | −1.989062 | 2.324251 |
| 6 | −0.836888 | −2.669301 | 2.228158 |
| 1 | 3.079230 | −3.239322 | 3.966664 |
| 1 | −0.060025 | −2.699958 | 1.491785 |
| 8 | 0.700509 | −2.942047 | −2.988099 |
| 1 | −0.989692 | −2.490283 | 4.883523 |
| 1 | 2.540508 | −1.081323 | 2.889370 |
| 6 | −5.352072 | −0.883969 | −2.965273 |
| 6 | −4.127589 | −1.027439 | −2.319888 |
| 6 | −0.844878 | −1.519763 | 4.449786 |
| 6 | −0.697732 | −1.413185 | 3.067121 |
| 1 | −1.803572 | −0.822619 | −1.350512 |
| 6 | −5.896577 | 0.367679 | −3.189721 |
| 6 | −3.453268 | 0.125184 | −1.920689 |
| 8 | −2.199869 | 0.043144 | −1.314525 |
| 6 | −0.822974 | −0.403669 | 5.265315 |
| 8 | −0.175025 | 0.006041 | 1.142576 |
| 6 | −0.484975 | −0.142783 | 2.533047 |
| 6 | −5.223079 | 1.494533 | −2.745840 |
| 6 | −3.997093 | 1.395338 | −2.098390 |
| 1 | −0.915605 | 0.289783 | 0.595380 |
| 1 | 6.067595 | 3.756774 | 1.419228 |
| 6 | −0.705766 | 0.853022 | 4.697660 |
| 1 | 6.288762 | 1.327129 | 1.926026 |
| 1 | −5.653084 | 2.465325 | −2.902021 |
| 6 | −0.562028 | 1.005733 | 3.323114 |
| 6 | 5.271076 | 3.075305 | 1.198084 |
| 6 | 5.398825 | 1.721536 | 1.481453 |
| 8 | 1.688339 | 4.846766 | 1.212197 |
| 1 | −0.745604 | 1.726516 | 5.318681 |
| 1 | −2.291700 | 2.681093 | −1.942671 |
| 6 | −3.303305 | 2.636390 | −1.570762 |
| 1 | 3.976708 | 4.576020 | 0.391612 |
| 6 | 4.105785 | 3.541022 | 0.613774 |
| 8 | −0.897026 | 3.003098 | −0.076913 |
| 6 | −3.274056 | 2.667943 | −0.051807 |

TABLE 6-continued

Cartesian coordinates of UHF/3-21G optimized [Ni-L']$^{2+}$

| Z | x | y | z |
|---|---|---|---|
| 6 | −2.075466 | 2.755237 | 0.644616 |
| 1 | −3.826087 | 3.508957 | −1.946274 |
| 6 | −0.637692 | 2.389257 | 2.710174 |
| 1 | 0.159974 | 2.514843 | 2.000422 |
| 6 | 4.350535 | 0.887133 | 1.167557 |
| 6 | −1.987048 | 2.570107 | 2.020639 |
| 1 | −5.382903 | 2.471414 | 0.188935 |
| 6 | −4.439242 | 2.532970 | 0.694373 |
| 6 | 1.156857 | 4.126208 | 0.392309 |
| 6 | 3.082093 | 2.642776 | 0.351738 |
| 1 | 4.418298 | −0.165327 | 1.336080 |
| 6 | −3.175045 | 2.446122 | 2.733732 |
| 6 | −4.394438 | 2.459016 | 2.077596 |
| 1 | −3.145447 | 2.319132 | 3.798252 |
| 7 | 3.206332 | 1.338259 | 0.625750 |
| 1 | −0.499761 | 3.131915 | 3.485427 |
| 6 | −0.301603 | 4.299160 | 0.043735 |
| 7 | 1.851523 | 3.072112 | −0.215303 |
| 1 | −0.431623 | 4.844127 | −0.879211 |
| 1 | −0.746583 | 4.867203 | 0.845005 |
| 6 | 1.400112 | 2.539990 | −1.455692 |
| 7 | 1.140102 | 1.235328 | −1.539658 |
| 1 | 1.538547 | 4.410562 | −2.467752 |
| 6 | 1.256831 | 3.380709 | −2.544702 |
| 6 | 0.668743 | 0.733618 | −2.689090 |
| 1 | 0.479384 | −0.316985 | −2.724944 |
| 6 | 0.757873 | 2.865125 | −3.731619 |
| 6 | 0.444321 | 1.517534 | −3.801815 |
| 1 | 0.629549 | 3.502021 | −4.583828 |
| 1 | 0.052786 | 1.079551 | −4.695793 |
| 1 | −5.304293 | 2.377032 | 2.638559 |
| 1 | −6.837856 | 0.464554 | −3.692959 |
| 1 | −5.477281 | −3.175897 | 2.153840 |
| 1 | −0.929663 | −0.508725 | 6.326825 |
| 28 | 1.749413 | −0.065357 | −0.009966 |

TABLE 7

Cartesian coordinates of UHF/3-21G optimized [Zn-L']$^{2+}$

| Z | x | y | z |
|---|---|---|---|
| 1 | −6.915432 | 2.846078 | −2.377125 |
| 6 | −5.955210 | 2.848138 | −1.905080 |
| 1 | −5.569296 | 4.928697 | −2.227152 |
| 1 | −5.986379 | 0.763499 | −1.419061 |
| 6 | −5.199079 | 4.010014 | −1.818747 |
| 6 | −5.443066 | 1.684164 | −1.370169 |
| 6 | −3.958895 | 3.976422 | −1.193526 |
| 7 | −4.239933 | 1.652756 | −0.778168 |
| 1 | −3.350962 | 4.852146 | −1.109376 |
| 6 | −3.514305 | 2.776097 | −0.685202 |
| 1 | −1.926928 | 4.266755 | 2.123966 |
| 1 | 0.388429 | 3.704807 | 0.148329 |
| 1 | 0.112119 | 2.144434 | 0.918571 |
| 7 | −2.255739 | 2.648806 | −0.027835 |
| 1 | 4.972496 | 3.090333 | −3.019856 |
| 1 | −1.801428 | 3.455575 | 4.474643 |
| 6 | −2.048167 | 3.229807 | 2.358649 |
| 1 | 2.822033 | 2.430533 | −4.063152 |
| 6 | 5.096763 | 3.653872 | −0.967640 |
| 6 | 4.470545 | 3.102759 | −2.072314 |
| 6 | 0.201098 | 2.650228 | −0.023591 |
| 6 | −1.974650 | 2.766283 | 3.672926 |
| 6 | −2.254326 | 2.312483 | 1.359049 |
| 1 | 4.966078 | 4.032154 | 1.117548 |
| 6 | 4.462820 | 3.632579 | 0.258868 |
| 6 | 3.198427 | 2.559041 | −1.969384 |
| 6 | −1.083499 | 2.556039 | −0.806552 |
| 1 | 2.949303 | 3.973650 | 2.333109 |
| 6 | 2.572634 | 1.866306 | −3.173719 |
| 1 | 1.495650 | 1.867848 | −3.095811 |
| 7 | −2.439532 | 1.005428 | 1.614830 |

TABLE 7-continued

Cartesian coordinates of UHF/3-21G optimized [Zn-L']²⁺

| Z | x | y | z |
|---|---|---|---|
| 6 | 3.187599 | 3.089083 | 0.422709 |
| 6 | 2.562841 | 2.602079 | −0.727555 |
| 6 | −2.105990 | 1.412861 | 3.927945 |
| 1 | 4.572475 | 1.023150 | −4.780855 |
| 8 | 1.258485 | 2.058976 | −0.735711 |
| 6 | −2.346174 | 0.551443 | 2.869641 |
| 6 | 2.643865 | 3.051145 | 1.854254 |
| 1 | −2.021518 | 1.025286 | 4.921368 |
| 1 | 1.571106 | 3.039700 | 1.888846 |
| 8 | −1.174754 | 2.433753 | −2.010180 |
| 1 | 4.669050 | 3.069389 | 3.650499 |
| 1 | −2.445544 | −0.502556 | 3.016003 |
| 6 | 4.178582 | 0.211784 | −4.199069 |
| 6 | 3.110902 | 0.450032 | −3.338816 |
| 6 | 4.233105 | 2.092499 | 3.562676 |
| 6 | 3.170126 | 1.895943 | 2.689872 |
| 1 | 1.371500 | 0.377943 | −1.399165 |
| 6 | 4.735187 | −1.048859 | −4.322037 |
| 6 | 2.605579 | −0.625121 | −2.608640 |
| 8 | 1.488833 | −0.487436 | −1.796535 |
| 6 | 4.735186 | 1.048785 | 4.322082 |
| 8 | 1.488915 | 0.487428 | 1.796459 |
| 6 | 2.605622 | 0.625094 | 2.608620 |
| 6 | 4.233062 | −2.092561 | −3.562643 |
| 6 | 3.170062 | −1.895980 | −2.689870 |
| 1 | 1.371609 | −0.377943 | 1.399066 |
| 1 | −5.569441 | −4.928583 | 2.227159 |
| 6 | 4.178556 | −0.211846 | 4.199098 |
| 1 | −6.915514 | −2.845923 | 2.377133 |
| 1 | 4.668992 | −3.069459 | −3.650449 |
| 6 | 3.110896 | −0.450070 | 3.338813 |
| 6 | −5.199197 | −4.009911 | 1.818753 |
| 6 | −5.955293 | −2.848012 | 1.905087 |
| 8 | −1.174835 | −2.433773 | 2.010186 |
| 1 | 4.572412 | −1.023219 | 4.780899 |
| 1 | 1.571006 | −3.039694 | −1.888845 |
| 6 | 2.643765 | −3.051169 | −1.854254 |
| 1 | −3.351106 | −4.852098 | 1.109380 |
| 6 | −3.959013 | −3.976356 | 1.193530 |
| 8 | 1.258410 | −2.059006 | 0.735722 |
| 6 | 3.187506 | −3.089125 | −0.422713 |
| 6 | 2.562762 | −2.602118 | 0.727557 |
| 1 | 2.949179 | −3.973681 | −2.333112 |
| 6 | 2.572591 | −1.866332 | 3.173715 |
| 1 | 1.495608 | −1.867846 | 3.095809 |
| 6 | −5.443115 | −1.684053 | 1.370174 |
| 6 | 3.198361 | −2.559084 | 1.969379 |
| 1 | 4.965969 | −4.032213 | −1.117569 |
| 6 | 4.462721 | −3.632636 | −0.258884 |
| 6 | −1.083579 | −2.556040 | 0.806555 |
| 6 | −3.514388 | −2.776045 | 0.685205 |
| 1 | −5.986401 | −0.763373 | 1.419066 |
| 6 | 4.470473 | −3.102818 | 2.072299 |
| 6 | 5.096674 | −3.653939 | 0.967619 |
| 1 | 4.972434 | −3.090396 | 3.019836 |
| 7 | −4.239983 | −1.652682 | 0.778171 |
| 1 | 2.821977 | −2.430565 | 4.063148 |
| 6 | 0.201018 | −2.650246 | 0.023598 |
| 7 | −2.255819 | −2.648789 | 0.027837 |
| 1 | 0.112048 | −2.144446 | −0.918560 |
| 1 | 0.388337 | −3.704827 | −0.148327 |
| 6 | −2.254398 | −2.312468 | −1.359047 |
| 7 | −2.439565 | −1.005407 | −1.614829 |
| 1 | −1.927059 | −4.266750 | −2.123964 |
| 6 | −2.048267 | −3.229798 | −2.358648 |
| 6 | −2.346196 | −0.551426 | −2.869640 |
| 1 | −2.445535 | 0.502576 | −3.016003 |
| 6 | −1.974738 | −2.766277 | −3.672925 |
| 6 | −2.106039 | −1.412851 | −3.927944 |
| 1 | −1.801538 | −3.455574 | −4.474641 |
| 1 | −2.021557 | −1.025279 | −4.921368 |
| 30 | −3.253865 | 0.000022 | 0.000001 |
| 1 | 6.075411 | −4.081418 | 1.059210 |
| 1 | 5.551997 | −1.215300 | −4.996015 |
| 1 | 6.075503 | 4.081341 | −1.059240 |
| 1 | 5.551979 | 1.215208 | 4.996086 |

The single point energy analysis of the optimized complexes yielded stabilization energies (ΔE) of −453.0 and −408.4 kcal/mol for $Ni^{2+}$ and $Zn^{2+}$ complexes, respectively, with the calculations performed at HF/3-21G. These were found to be −450.1 and −408.4 kcal/mol, respectively, at HF/6-31G level. The stabilization energies were found to be well within the formation of 5- or 4-coordination bonds with $Ni^{2+}$ or $Zn^{2+}$.

Stabilisation Energy Calculation $$\Delta E = E_a - (E_b - E_c)$$

Where $E_a$ = Energy of the complex i.e., [Ni-L']²⁺ or [Zn-L']²⁺ or $Ni^{2+}$—$Zn^{2+}$-L"

$E_b$ = Energy of the Ligand as it present in the complex, i.e., L' or L"

$E_c$ = Energy of the cation in the case of mono-metallic complexes and sum of energy of cations in case of bi-metallic complexes i.e. $E_{Ni}^{2+}$ or $E_{Zn}^{2+}$ or $[E_{Ni}^{2+} + E_{Zn}^{2+}]$ All the energies are obtained by performing single point energy calculations at the same level of theory.

| Theory/basis set | System | $E_a$ in au | $E_b$ in au | $E_c$ in au | ΔE in au | ΔE in kcal/mol |
|---|---|---|---|---|---|---|
| UHF/3-21G | [Ni-L']²⁺ | −4274.75933600 | −2768.27287196 | −1505.76459499 | −0.72186905 | −453.0 |
| | [Zn-L']²⁺ | −4545.58116490 | −2768.31825459 | −1776.61206747 | −0.65084284 | −408.4 |
| UHF/6-31G | [Ni-L']²⁺ | −4274.75933600 | −2768.27748330 | −1505.76459500 | −0.71725770 | −450.1 |
| | [Zn-L']²⁺ | −4545.58116490 | −2768.31825460 | −1776.61206750 | −0.65084280 | −408.4 |

The calculation for [Ni-L']²⁺ and [Ni-L']²⁺ were done at UHF/6-31G level and the other two were done at UHF/3-21G||UHF/6-31G level.

Example 9

Synthesis of 1,3-bis(2-picolyl)amine Derivative of calix[4]arene (IX)

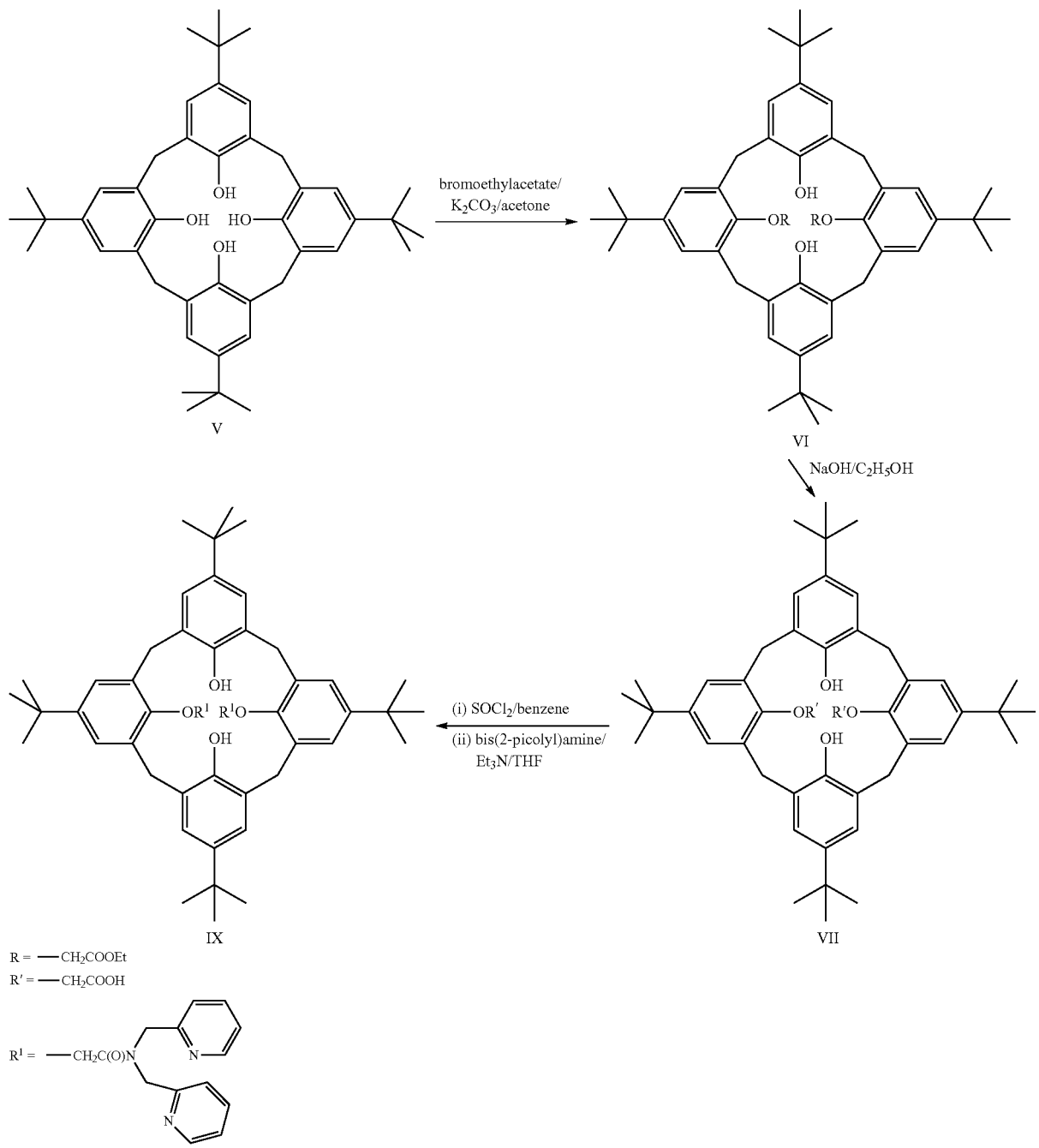

Scheme 3

R = —CH$_2$COOEt
R' = —CH$_2$COOH
R$^1$ = —CH$_2$C(O)N(CH$_2$-2-pyridyl)$_2$

Compounds V, VI, and VII were prepared as shown in Example 1 above.

Synthesis and Characterization of IX:

A suspension of bis(2-picolyl)amine (0.59 g, 2.96 mmol) and Et$_3$N (0.55 g, 5.43 mmol) were stirred in dry THF (30 mL) under argon atmosphere. 1,3-diacid chloride derivative of calix[4]arene, (1.08 g, 1.35 mmol) in dry THF (30 mL) was added drop wise to this reaction mixture. Immediately, a yellowish precipitate was formed and stirring was continued for 48 h at room temperature. After filtration, the filtrate was concentrated to dryness. A yellow solid was obtained which was extracted with CHCl$_3$, washed with water and then with brine and the organic layer was dried with anhydrous Na$_2$SO$_4$. Filtrate was concentrated to dryness and purified by column chromatography using $CH_2Cl_2$ and $CH_3OH$ as eluents (9.0:1.0) which results in the final product as white solid.

Yield (35%, 0.52 g);

$C_{72}H_{82}N_6O_6$ (1127.50): Anal. (% found) C, 75.18; H, 7.34; N, 7.34, $C_{72}H_{82}N_6O_6$. $C_2H_5OH$ (% requires) C, 75.71; H, 7.56; N, 7.16);

FTIR: (KBr, $cm^{-1}$): 1641 ($v_{C=O}$), 3394 ($v_{OH}$);

$^1H$ NMR: ($CDCl_3$, δ ppm): 0.93 (s, 18H, $C(CH_3)_3$), 1.27 (s, 18H, $C(CH_3)_3$), 3.27 (d, 4H, Ar—$CH_2$—Ar, J=13.14 Hz), 4.34 (d, 4H, Ar—$CH_2$—Ar, J=13.14 Hz), 4.71, 4.94 (s, 8H, $NCH_2$), 4.97 (s, 4H, $OCH_2$), 6.76 (s, 4H, Ar—H), 7.02 (s, 4H, Ar—H), 7.04 (t, 2H, Py-H, J=6.40 Hz), 7.13 (t, 2H, Py-H, J=6.42 Hz), 7.25-7.27 (m, 2H, Py-H), 7.40 (d, 2H, Py-H, J=7.90 Hz), 7.51-7.58 (m, 6H, Py-H and OH), 8.41 (d, 2H, Py-H, J=4.88 Hz) 8.52 (d, 2H, Py-H, J=4.88 Hz);

$^{13}C$ NMR: ($CDCl_3$, 100 MHz δ ppm): 31.1, 31.8 ($C(CH_3)_3$), 31.9 (Ar—$CH_2$—Ar), 33.9, 34.0 ($C(CH_3)_3$), 51.4, 52.2 ($NCH_2$), 74.5 ($OCH_2CO$), 122.2, 122.25, 122.5, 125.1, 125.7, 127.9, 132.7, 136.7, 136.9, 141.3, 147.3, 148.9, 149.9, 150.8, 156.4, 157.3 (Py-C and calix-Ar—C), 169.2 (C=O);

m/z (ES-MS) 1127.78 ([M]+70%), 1128.80 ([M+H]+ 40%).

Example 10

Metal Ion Binding of 1,3-bis(2-picolyl)amine Derivative of calix[4]arene (IX)

The metal ion binding of IX and its control molecules were studied by fluorescence spectroscopy. The metal ions, eg., $Mn^{2+}$, $Fe^{2+}$, $Co^{2+}$, $Ni^{2+}$, $Cu^{2+}$, $Zn^{2+}$, $Na^+$, $K^+$, $Ca^{2+}$, and $Mg^{2+}$, were subjected to recognition studies with IX and the control molecules. The studies were carried out by exciting the solutions at 285 nm and recording the fluorescence spectra in the range of 295-420 nm in methanol as well as in 1:1 aqueous methanol.

Figure 11:
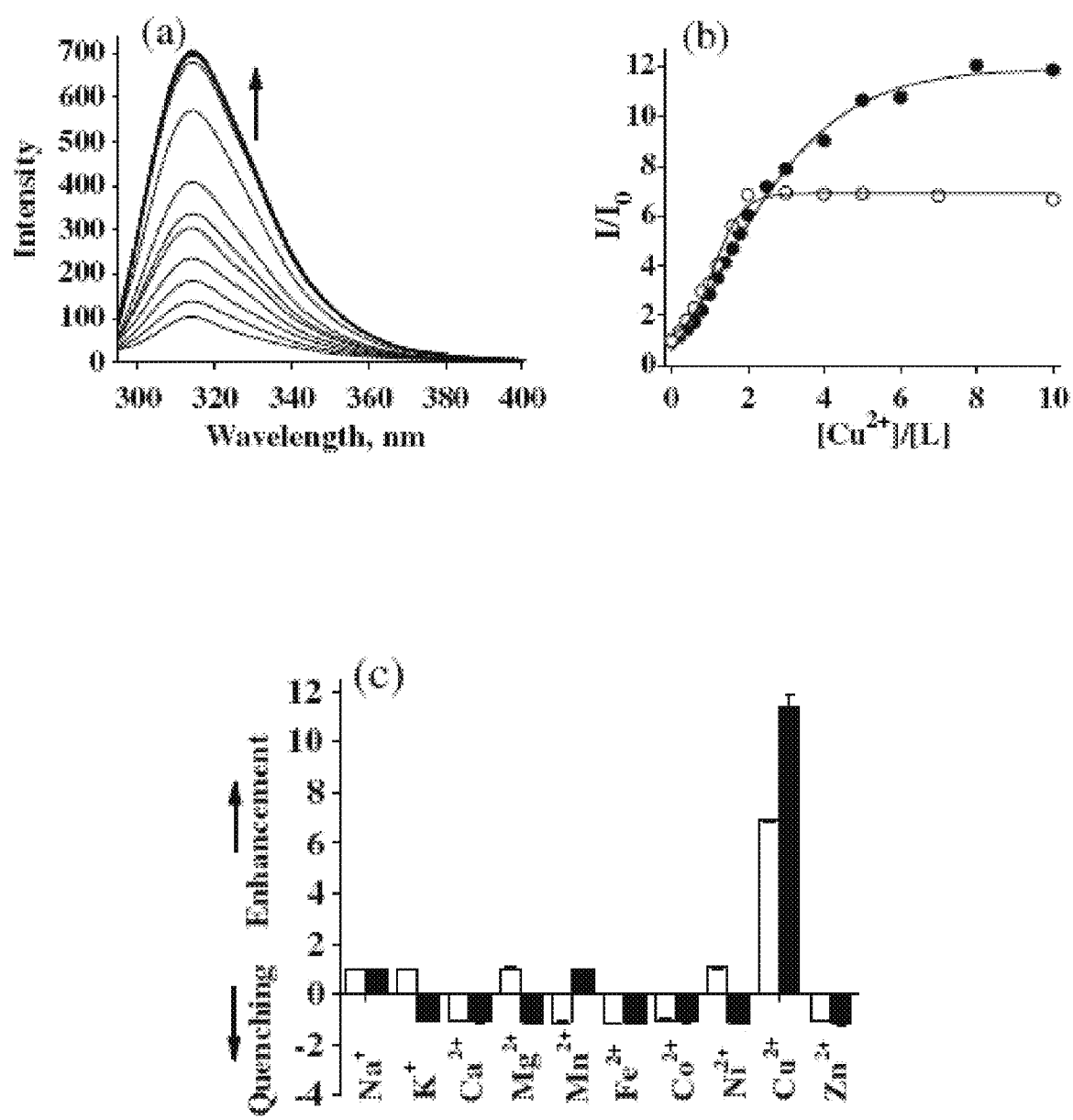
FIG. 11 depicts an illustrative embodiment of a Fluorescence titration of 1,3-bis(2-picolyl)amine derivative of calix[4]arene (IX, shown as L in the figure) with different metal ions: (a) spectral traces during the titration of IX with $Cu^{2+}$ in methanol, (b) plot of relative fluorescence intensity versus number of equivalents of $Cu^{2+}$ added in methanol (unfilled) and in 1:1 aqueous methanol (filled), and (c) histogram representing the fluorescence enhancement and quenching fold exhibited by IX with different metal ions studied in methanol (unfilled) and in 1:1 aqueous methanol (filled).

During the titration in methanol, the fluorescence intensity of IX increases as a function of $Cu^{2+}$ addition (FIG. 11a) and shows about 7 fold enhancement and saturates around 2 equiv of $Cu^{2+}$ addition (FIG. 11b). Thus the titration of IX with $Cu^{2+}$ results in a stoichiometric reaction. However, when similar titrations were carried out with other metal ions, such as, $Mn^{2+}$, $Fe^{2+}$, $Co^{2+}$, $Ni^{2+}$, $Zn^{2+}$, $Na^+$, $K^+$, $Ca^{2+}$, and $Mg^{2+}$, only a minimal enhancement or minimal quenching was observed (FIG. 11c).

Since aqueous solutions are desirable in order to have a wide range of applicability of the receptor, similar titrations were carried out in 1:1 aqueous methanol and a ~12 fold increase in the fluorescence intensity of IX with $Cu^{2+}$ (FIG. 11b and c) was found though the saturation was found around 5-6 equiv. The observed enhancement in the fluorescence intensity may be explained to be the reversal of PET when $Cu^{2+}$ binds to the nitrogens of pyridyl moieties. The binding constant of IX with $Cu^{2+}$ was calculated by Benesi-Hildebrand equation and the corresponding association constant, $K_a$ was found to be 17,547±1000 and 30,221±1600 $M^{-1}$, respectively, in methanol and 1:1 aqueous methanol. The quantum yield of IX and its complex with $Cu^{2+}$ were found to be 0.0118 and 0.0559 in methanol and 0.0127 and 0.0980 in aqueous methanol with respect to naphthalene as standard.

Example 11

Absorption Titrations of 1,3-bis(2-picolyl)amine Derivative of calix[4]arene (IX)

Figure 12:
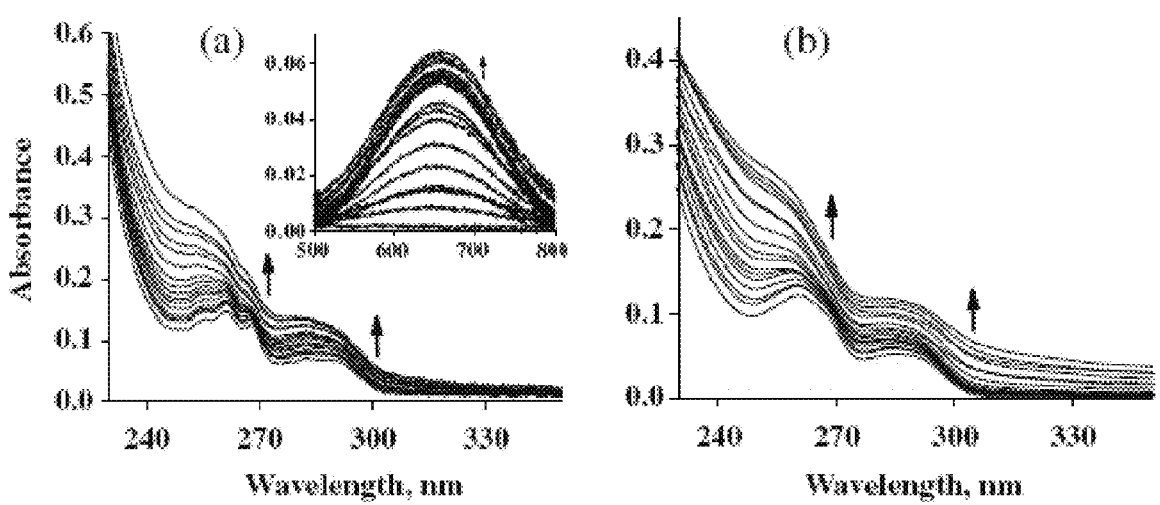
FIG. 12 depicts an illustrative embodiment of a absorption spectral titration of IX (shown as L in the figure) with $Cu^{2+}$: (a) spectral traces observed during the titration in the region 230-350 nm, inset shows the spectral traces in the region 500-800 nm as measured at a higher concentration in methanol, and (b) spectral traces observed in aqueous methanol medium.

In order to support the binding of IX by $Cu^{2+}$, absorption titrations were carried out. The spectral changes were suggestive of binding of $Cu^{2+}$ with IX (FIG. 12). Absorption spectra recorded at higher concentrations exhibited a d-d transition band at 655 nm which also demonstrates the interaction of ligand with metal ion (FIG. 12a, inset). Plot of absorbance versus added [$Cu^{2+}$] clearly indicated the formation of the complex (FIG. 13a) and the complex formed was found to be 1:1 based on Job's plot (FIG. 13b) in both the solvent systems.

Figure 13:
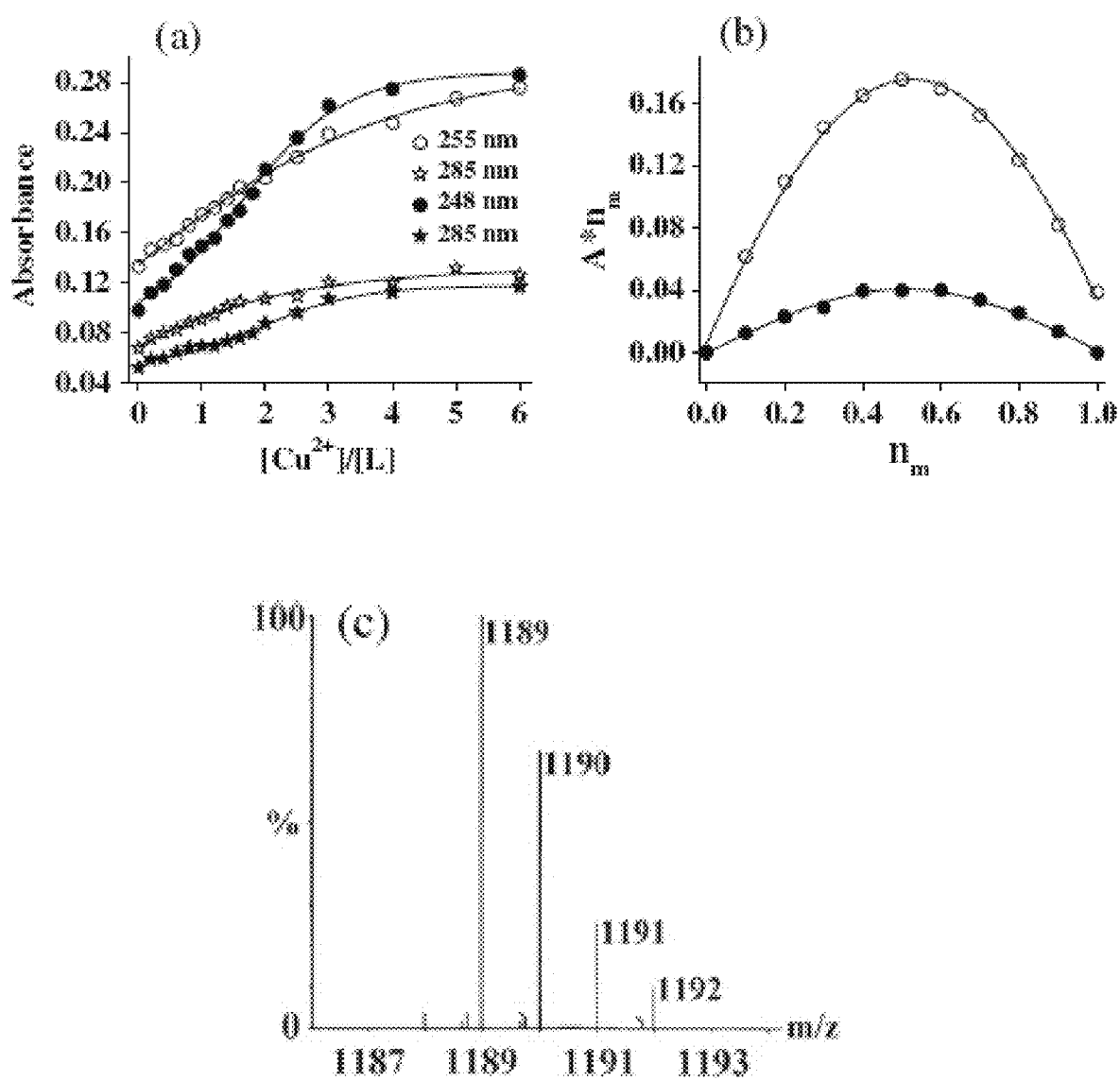
FIG. 13 depicts an illustrative embodiment of: (a) absorbance versus mole ratio of $[Cu^{2+}]/[L]$ added in methanol (unfilled) and in 1:1 aqueous methanol (filled) (1,3-bis(2-picolyl)amine derivative of calix[4]arene IX shown as L in the figure), (b) Job's plot of $n_m$ versus $A*n_m$, where $n_m$ is mole fraction of the metal ion added and A is absorbance as studied in methanol (unfilled) and aqueous methanol (filled), and (c) molecular ion peak indicating the isotopic peak pattern for the $Cu^{2+}$ complex of IX as obtained from ESI mass spectrum.

The 1:1 stoichiometry of the complex was further supported based on the molecular ion peak observed at m/z value of 1189 in ESI MS titration (FIG. 13c). The isotopic peak pattern provides an unambiguous assignment to this peak by confirming the presence of $Cu^{2+}$ in the complex. The minimum concentration at which IX can detect $Cu^{2+}$ under the present conditions has been found to be 196 ppb in methanol and 341 ppb in aqueous methanol.

Example 12

Comparative Metal Ion Binding of 1,3-bis(2-picolyl)amine Derivative of calix[4]arene (IX)

Figure 14:
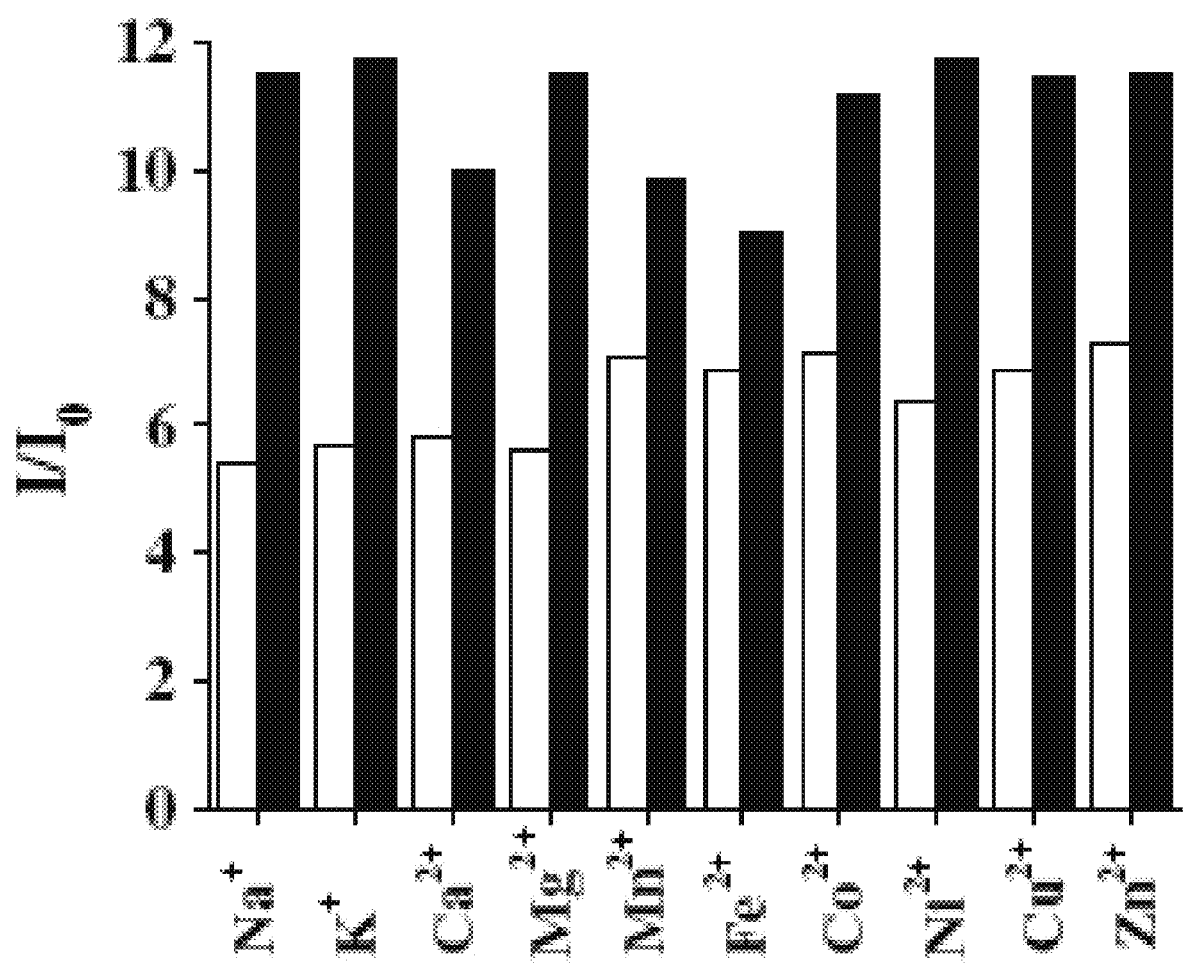
FIG. 14 depicts an illustrative embodiment of a relative fluorescence intensity of IX upon the addition of 3 equiv of $Cu^{2+}$ in the presence of 30 equiv of $Na^+$, $K^+$, $Ca^{2+}$, and $Mg^{2+}$ and 5 equiv of $Mn^{2+}$, $Fe^{2+}$, $Co^{2+}$, $Ni^{2+}$, and $Zn^{2+}$, carried out in methanol (unfilled) and in 1:1 aqueous methanol (filled).

The competition of $Cu^{2+}$ toward IX against other metal ions was studied by titrating a solution containing IX and $M^{n+}$ in 1:30 ratio in the case of $Na^+$, $K^+$, $Ca^{2+}$, $Mg^{2+}$ and 1:5 ratio in the case of $Mn^{2+}$, $Fe^{2+}$, $Co^{2+}$, $Ni^{2+}$, $Zn^{2+}$ with $Cu^{2+}$ of different concentrations. These studies resulted in no significant change in the fluorescence intensity observed with the {IX+$Cu^{2+}$} species and thereby revealed that the $Cu^{2+}$ could replace $M^{n+}$. This conforms to the strong binding nature of IX toward $Cu^{2+}$ in the presence of other $M^{n+}$ ions (FIG. 14, IX shown as L in the figure).

Example 13

Binding Core of 1,3-bis(2-picolyl)amine Derivative of calix[4]arene (IX)

Figure 15:
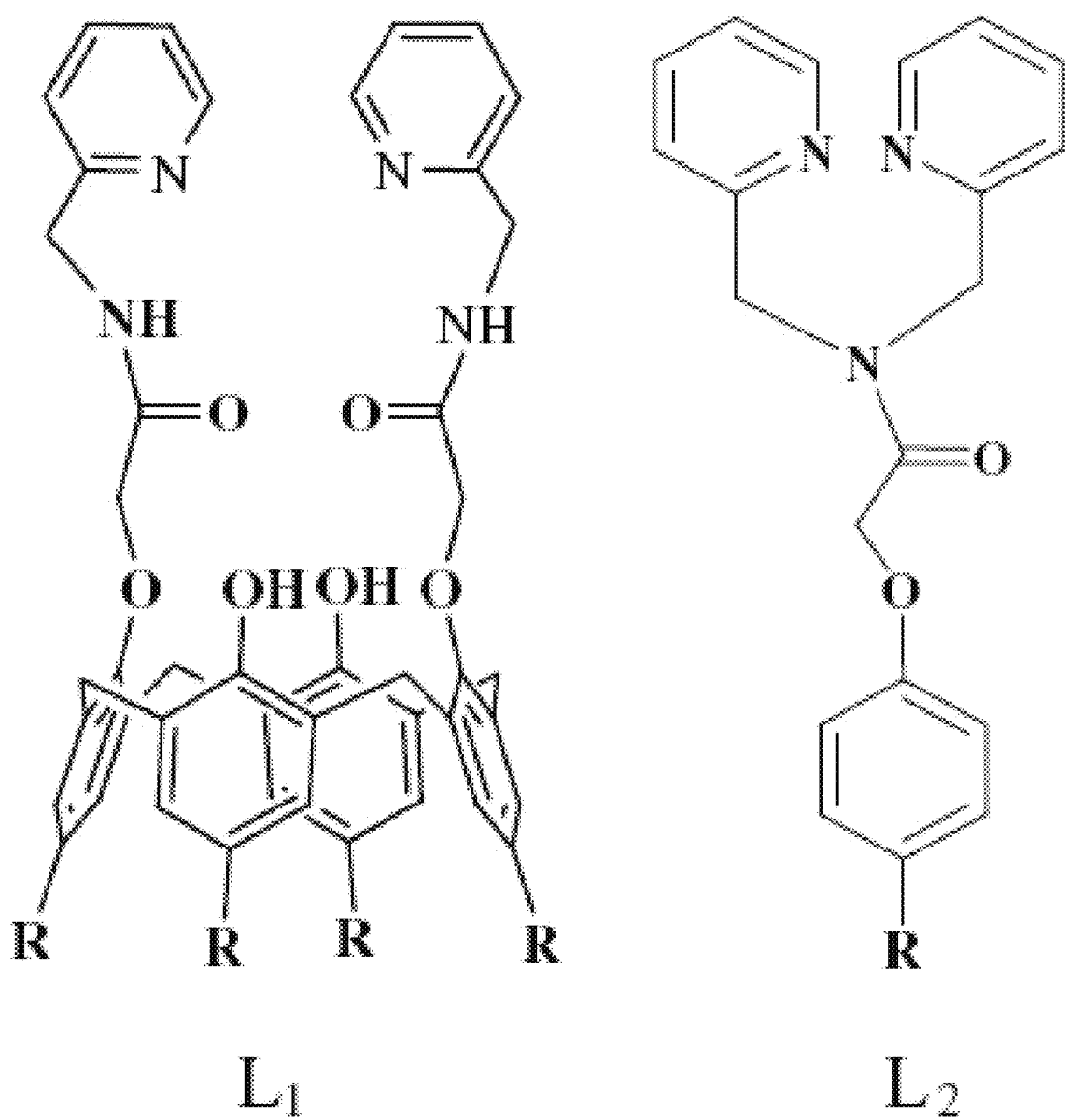
FIG. 15 depicts an illustrative embodiment of schematic structures of the control molecules $L_1$ and $L_2$. R=tert-butyl.

The role of calix[4]arene platform and the pre-organized nitrogen core in the recognition process has been proven by studying fluorescence properties of the reference molecules (FIG. 15), viz., $L_1$ and $L_2$ with different metal ions. The control molecule $L_1$ possessing the calixarene moiety has been prepared by the same method as for compound IX by coupling diacid chloride derivative of calix[4]arene with 2-aminomethyl pyridine (see Joseph, R. et al, *J. Org. Chem.* 2008, 73, 5745).

On the other hand, $L_2$, a molecular system that has only one strand of IX without any calixarene platform, has been synthesized by using p-tert-butyl phenol as starting material instead of calix[4]arene (see Joseph, R. et al, supra). Yield (43%, 0.40 g). $C_{24}H_{27}N_3O_2$ (389.48): Anal. (% found) C, 73.80; H, 6.89; N, 11.20, $C_{24}H_{27}N_3O_2$ (% requires) C, 74.00; H, 6.98; N, 10.78). FTIR: (KBr, $cm^{-1}$): 1660 ($v_{C=O}$). 1H NMR: ($CDCl_3$, δ ppm): 1.21 (s, 9H, $C(CH_3)_3$), 4.68 (d, 4H, $NCH_2$, J=8.55 Hz), 4.88 (s, 2H, $OCH_2$), 6.79 (d, 2H, Ar—H, J=9.17 Hz), 7.08 (t, 1H, Py-H, J=5.04 Hz), 7.13 (t, 2H, Py-H, J=6.87 Hz), 7.16-7.21 (m, 3H, Ar—H and Py-H), 7.50 (t, 1H, Py-H, J=7.63 Hz), 7.55 (t, 1H, Py-H, J=7.79 Hz), 8.40 (d, 1H, Py-H, J=6.42 Hz), 8.50 (d, 1H, Py-H, J=5.81 Hz). $^{13}C$ NMR: ($CDCl_3$, 100 MHz δ ppm): 31.6 ($C(CH_3)_3$), 34.2 ($C(CH_3)_3$), 51.5, 52.4 ($NCH_2$), 67.6 ($OCH_2$), 114.3, 121.7, 122.5, 122.7, 126.8, 126.3, 136.8, 144.2, 149.2, 150.0, 155.9, 156.3, 157.1 (Ar—C and Py-C), 169.4 (C=O).

m/z (ES-MS) 390.16 ([M+H]$^+$ 100%).

Figure 16:
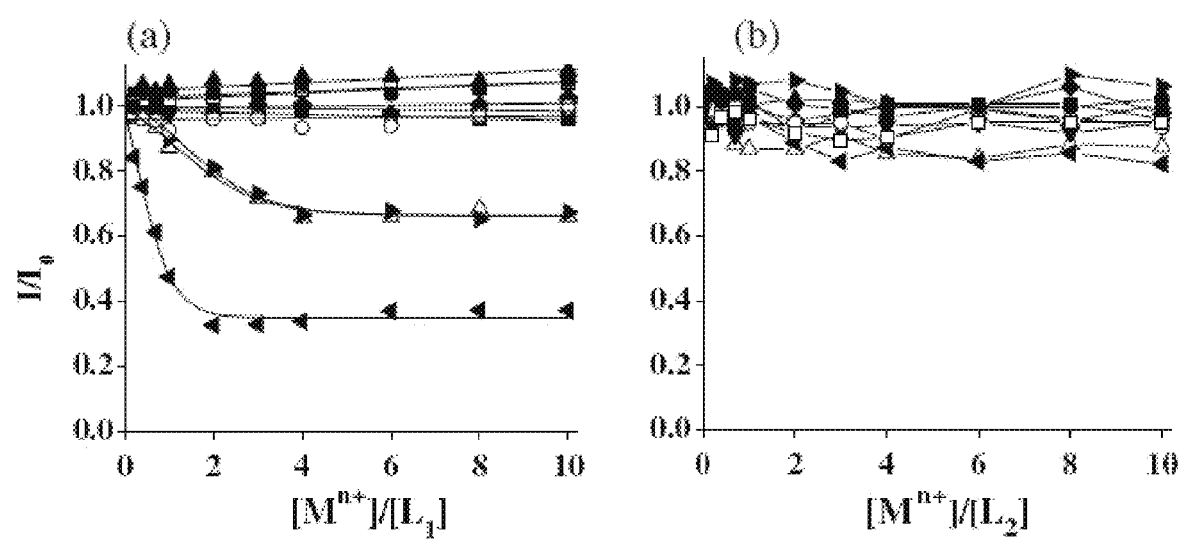
FIG. 16 depicts an illustrative embodiment of plots of $(I/I_o)$ as a function of metal to the ligand mole ratio during the fluorescence titration in methanol, (a) $L_1$, (b) $L_2$. The symbols corresponds to ■=$Mn^{2+}$; ∆=$Fe^{2+}$; ▲=$Co^{2+}$; ▼=$Ni^{2+}$; ◄=$Cu^{2+}$; ►=$Zn^{2+}$; ♦=$Na^+$; ○=$K^+$; □=$Ca^{2+}$; ●=$Mg^{2+}$.

The L₁ contains a methylpyridine moiety instead of two pyridine moieties that are present in compound IX. The role of calix[4]arene platform in the selective binding of $Cu^{2+}$ with IX has been further established by studying the metal ion binding properties of $L_2$. The fluorescence titration studies of $L_1$ showed no selectivity toward any metal ions, while $Fe^{2+}$, $Zn^{2+}$, and $Cu^{2+}$ exhibited a fluorescence quenching (FIG. 16a). Though $Cu^{2+}$ exhibited a minimal fluorescence quenching of 2.8 fold, such minimal response is not sufficient enough to detect a particular $M^{n+}$ ion and hence reflects on the lack of pre-organized binding core. The lack of calix[4]arene platform makes $L_2$ a non-selective molecule toward all the metal ions studied (FIG. 16b). The results obtained from the control molecules suggest that a pre-organized hetero core is required for $Cu^{2+}$ binding. However, IX contains two picolyl moieties and a calixarene platform that makes it suitable for selective binding.

Example 14

Computational Calculations

In order to understand the structural features of the 1:1 complex formed between IX and $Cu^{2+}$, computational calculations were carried out at HF/3-21G followed by HF/6-31G levels using GAUSSIAN 0313 package.
Frisch, M. J.; Trucks, G. W.; Schlegel, H. B.; Scuseria, G. E.; Robb, M. A.; Cheeseman, J. R.; Montgomery, J. A., Jr.; Vreven, T.; Kudin, K. N.; Burant, J. C.; Millam, J. M.; Iyengar, S. S.; Tomasi, J.; Barone, V.; Mennucci, B.; Cossi, M.; Scalmani, G.; Rega, N.; Petersson, G. A.; Nakatsuji, H.; Hada, M.; Ehara, M.; Toyota, K.; Fukuda, R.; Hasegawa, J.; Ishida, M.; Nakajima, T.; Honda, Y.; Kitao, O.; Nakai, H.; Klene, M.; Li, X.; Knox, J. E.; Hratchian, H. P.; Cross, J. B.; Adamo, C.; Jaramillo, J.; Gomperts, R.; Stratmann, R. E.; Yazyev, O.; Austin, A. J.; Cammi, R.; Pomelli, C.; Ochterski, J. W.; Ayala, P. Y.; Morokuma, K.; Voth, G. A.; Salvador, P.; Dannenberg, J. J.; Zakrzewski, V. G.; Dapprich, S.; Daniels, A. D.; Strain, M. C.; Farkas, O.; Malick, D. K.; Rabuck, A. D.; Raghavachari, K.; Foresman, J. B.; Ortiz, J. V.; Cui, Q.; Baboul, A. G.; Clifford, S.; Cioslowski, J.; Stefanov, B. B.; Liu, G.; Liashenko, A.; Piskorz, P.; Komaromi, I.; Martin, R. L.; Fox, D. J.; Keith, T.; Al-Laham, M. A.; Peng, C. Y.; Nanayakkara, A.; Challacombe, M.; Gill, P. M. W.; Johnson, B.; Chen, W.; Wong, M. W.; Gonzalez, C.; Pople, J. A. *GAUSSIAN* 03, Revision C.02; Gaussian: Wallingford, Conn., 2004.

The computations were initiated by taking the coordinates of IX from its crystal structure and by replacing the tert-butyl moiety by a hydrogen atom to result in L'. The L' was optimized at both HF/3-21G and HF/6-31G before carrying out the computation for the complex. Even the DFT level computations carried out with 6-31G basis set exhibited same conformation as that obtained at HF/6-31G level. Computations for the complex species were initiated by placing the $Cu^{2+}$ at a non-interacting distance that is well above the pyridyl core of the derivative and optimized at HF/3-21G level and the output from this was taken through HF/6-31G.

Figure 17:
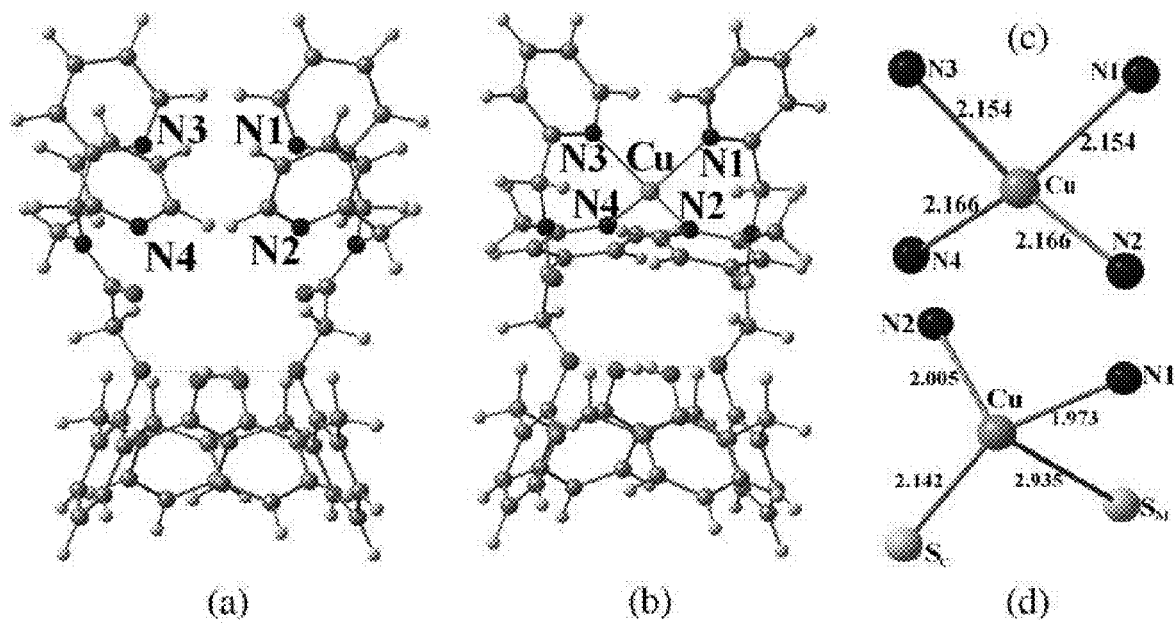
FIG. 17 depicts an illustrative embodiment of HF/6-31G optimized structure of (a) L', and (b) $[CuL']^{2+}$; (c) $Cu^{2+}$ coordination site as in (b), and (d) $Cu^{2+}$ coordination site from plastocyanin (PDB id: 1BXU). Coordination core angles in (°) for $Cu^{2+}$ in (c): N1-Cu—N2=89.8; N1-Cu—N3=92.1; N1-Cu—N4=128.4; N2-Cu—N3=128.4; N2-Cu—N4=127.2 and N3-Cu—N4=89.8. Coordination core angles in (°) for $Cu^{2+}$ in (d): N1-Cu—N2=101.4; N1-Cu—$S_M$=98.8; N1-Cu—$S_C$=121.4; N2-Cu—$S_M$=86.0; N2-Cu—$S_C$=131.0 and $S_M$-Cu—$S_C$=107.7.

Based on these calculations it was found that the formation of the complex was accompanied by an energy stabilization of −422.8 kcal/mol at HF/6-31G. The optimization brought the N4 core of the pyridyl moieties in L' into the coordination range (FIGS. 17a and b) and resulted in a tetra-coordinated $Cu^{2+}$ center where all the four pyridyl moieties were involved in binding. The coordination of $Cu^{2+}$ center is highly distorted tetrahedral where the angles range from 89° to 128° that is very much similar to that observed for the same in blue copper proteins, viz., plastocyanin (FIGS. 17c and d). Such highly distorted tetrahedral center observed for $Cu^{2+}$ in blue copper proteins has been interpreted to the ease with which the protein could fulfill the coordination requirement for $Cu^{1+}$ during the electron transfer process.

Example 15

Scanning Electron Microscopy (SEM) and Atomic Force Microscopy (AFM) Study

Figure 18:
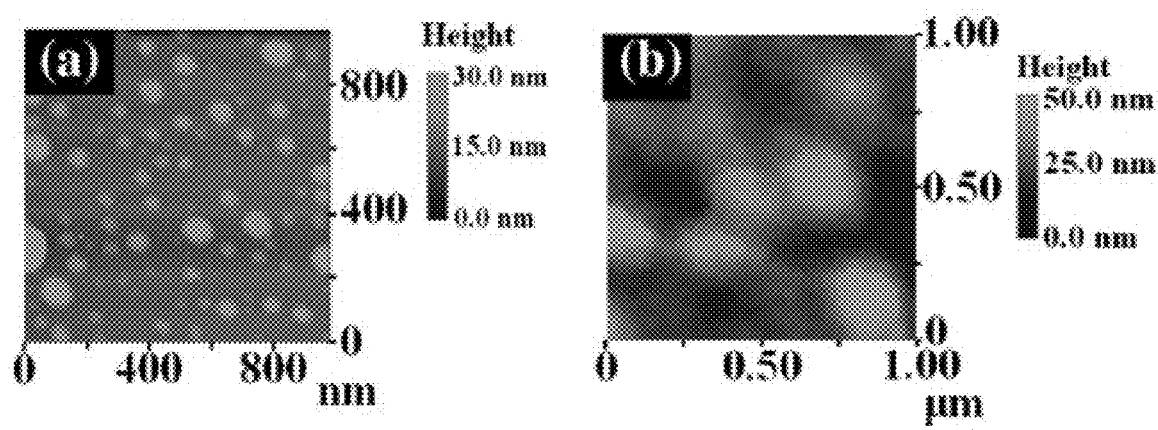
FIG. 18 depicts an illustrative embodiment of AFM (atomic force microscopy) images of (a) 1,3-bis(2-picolyl) amine derivative of calix[4]arene (IX) and (b) $Cu^{2+}$ complex of IX.

In order to confirm the structural changes that exist at nano level between the receptor IX and its $Cu^{2+}$ complex, studies were carried out by scanning electron microscopy (SEM) and atomic force microscopy (AFM). While IX showed rod-like structure of length varying from 4 to 20 μm, its $Cu^{2+}$ complex showed a smooth surface of smaller particles (1-2 μm) of irregular shape though these were approximately closer to spherical ones. AFM of IX showed spherical particles of three different sizes (FIG. 18). While the smallest one had a size of 37 nm and a height of 4 nm, the medium- and large-sized particles were exactly double and triple to this, respectively, indicating that the smallest unit showed little aggregation. However, this aggregation was severe in the $Cu^{2+}$ complex of IX leading to the formation of large-sized clusters with size >250 nm and height >35 nm. Thus IX and its $Cu^{2+}$ complex were distinguishable based on their SEM and AFM features.

EQUIVALENTS

The present disclosure is not to be limited in terms of the particular embodiments described in this application. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A compound of Formula I:

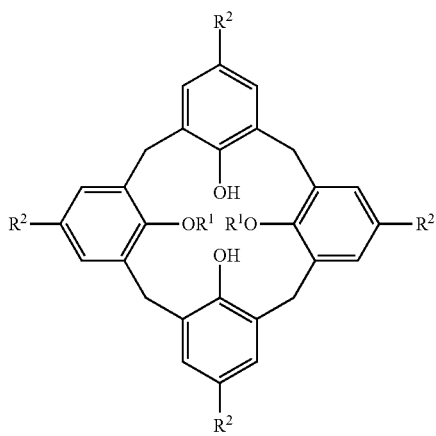

I or salts thereof, wherein
each $R^1$ independently is

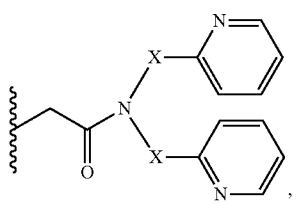

wherein X is —$CH_2$— or is absent, and each $R^2$ is independently a $C_{3-6}$ straight, branched or cyclic alkyl group.

2. The compound of claim 1, wherein each $R^2$ is a t-butyl.

3. The compound of claim 1 wherein X is $CH_2$.

4. The compound of claim 1 wherein X is absent.

5. A complex comprising a compound of claim 1 and a $Zn^{2+}$ ion.

6. A complex comprising a compound of claim 1 and a $Ni^{2+}$ ion.

7. A complex comprising a compound of claim 1 and a $Cu^{2+}$ ion.

8. A method of testing a sample for the presence of $Zn^{2+}$ ions, $Ni^{2+}$ ions, or a mixture thereof comprising:
combining a compound of claim 1, wherein X is absent, with a test sample, and
detecting a fluorescence of the test sample,
wherein an increase in the fluorescence of the test sample upon combination with said compound indicates the presence of $Zn^{2+}$ ions in the test sample and a decrease in the fluorescence of the test sample upon combination with said compound indicates the presence of $Ni^{2+}$ ions in the test sample.

9. The method of claim 8 further comprising comparing the detected fluorescence of the test sample with a fluorescence of a control sample, wherein an increase in the fluorescence of the test sample relative to the control sample indicates the presence of $Zn^{2+}$ ions in the test sample and a decrease in the fluorescence of the test sample relative to the control sample indicates the presence of $Ni^{2+}$ ions in the test sample.

10. The method of claim 8, wherein the test sample is an alcoholic solution.

11. The method of claim 10, wherein the alcoholic solution comprises methanol or ethanol.

12. The method of claim 11, wherein the method selectively detects the presence of $Zn^{2+}$ ions or $Ni^{2+}$ ions in the presence of one or more additional divalent metal ions.

13. The method of claim 12, wherein the one or more additional divalent metal ions are selected from the group consisting of $Co^{2+}$, $Cd^{2+}$, $Cu^{2+}$, $Fe^{2+}$, $Hg^{2+}$, and $Mn^{2+}$.

14. The method of claim 8 wherein the test sample includes a mixture of $Ni^{2+}$ and $Zn^{2+}$ ions in which the amount of $Ni^{2+}$ ions is at least ten times the amount of $Zn^{2+}$ ions or the amount of $Zn^{2+}$ ions is at least ten times the amount of $Ni^{2+}$ ions.

15. A method of testing a sample for the presence of $Cu^{2+}$ ions, comprising:
combining a compound of claim 1, wherein X is $CH_2$, with a test sample, and
detecting a fluorescence of the test sample,
wherein an increase in the fluorescence of the test sample upon combination with said compound indicates the presence of $Cu^{2+}$ ions in the test sample.

16. The method of claim 15 further comprising comparing the detected fluorescence of the test sample with the fluorescence of a control sample, wherein an increase in the fluorescence of the test sample relative to the control sample indicates the presence of $Cu^{2+}$ ions in the test sample.

17. The method of claim 16, wherein the test sample or the control sample is an alcoholic solution.

18. The method of claim 17, wherein the method selectively detects the presence of $Cu^{2+}$ ions in the presence of one or more additional mono- or divalent metal ions.

19. The method of claim 18, wherein the one or more additional divalent metal ions are selected from the group consisting of $Na^+$, $K^+$, $Ca^{2+}$, $Mg^{2+}$, $Mn^{2+}$, $Co^{2+}$, $Fe^{2+}$, $Hg^{2+}$, $Ni^{2+}$, $Zn^{2+}$, and $Mn^{2+}$ ions.

20. A method for preparing a compound of claim 1 comprising contacting 2,2'-dipyridylamine or bis(pyridin-2-ylmethyl)amine in a presence of a suitable base and a solvent with a compound of Formula II:

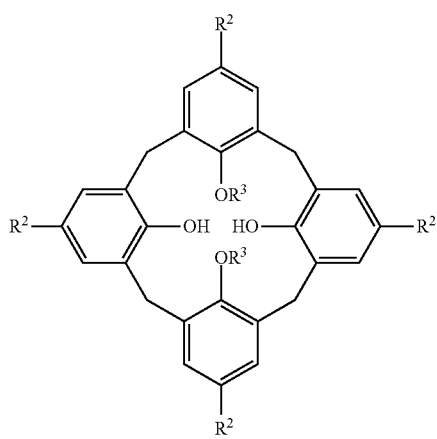

II wherein $R^3$ is —$CH_2COX$ and X is a halide.

* * * * *

UNITED STATES PATENT AND TRADEMARK OFFICE
CERTIFICATE OF CORRECTION

| | | |
|---|---|---|
| PATENT NO. | : 8,034,621 B2 | Page 1 of 1 |
| APPLICATION NO. | : 12/543348 | |
| DATED | : October 11, 2011 | |
| INVENTOR(S) | : Rao et al. | |

It is certified that error appears in the above-identified patent and that said Letters Patent is hereby corrected as shown below:

In Column 4, Line 21, delete "$n_m$," and insert -- $n_m$ --, therefor.

In Column 15, Line 36, delete "Volume/volume" and insert -- Volume/volume. --, therefor.

In Column 17, Line 41, delete "1H" and insert -- $^1H$ --, therefor.

In Column 17, Line 59, delete "1H" and insert -- $^1H$ --, therefor.

In Column 30, Line 49, delete "[$E_{Ni}^{2+}+E_{Zn}^{2+}$]" and insert -- [$E_{Ni}^{2+}+E_{Zn}^{2+}$]. --, therefor.

In Column 34, Line 56, delete "1H" and insert -- $^1H$ --, therefor.

In Column 37, Line 45, in Claim 3, delete "1" and insert -- 1, --, therefor.

In Column 37, Line 46, in Claim 4, delete "1" and insert -- 1,--, therefor.

In Column 38, Line 14, in Claim 14, delete "8" and insert -- 8, --, therefor.

Signed and Sealed this
First Day of May, 2012

David J. Kappos
*Director of the United States Patent and Trademark Office*